United States Patent
Sadlowski et al.

(10) Patent No.: US 8,367,598 B2
(45) Date of Patent: *Feb. 5, 2013

(54) WHITENING AGENTS FOR CELLULOSIC SUBTRATES

(75) Inventors: Eugene Steven Sadlowski, Cincinnati, OH (US); Mark Robert Sivik, Mason, OH (US); Michael David Cummings, West Chester, OH (US); Donna D'Angelo Morrall, West Harrison, IN (US); Kevin Lee Kott, Cincinnati, OH (US); Keith Homer Baker, Cincinnati, OH (US); Brian Joseph Loughnane, Fairfield, OH (US); Michael A Valenti, Greenville, SC (US); Laurent D Kieken, Greenville, SC (US); Xiayong Michael Hong, Greer, SC (US); Eduardo Torres, Boiling Springs, SC (US); Dominick J Valenti, Greenville, SC (US); Patrick D Moore, Pacolet, SC (US); Leonard J Starks, Duncan, SC (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/546,054

(22) Filed: Jul. 11, 2012

(65) Prior Publication Data

US 2012/0277139 A1 Nov. 1, 2012

Related U.S. Application Data

(63) Continuation of application No. 12/510,327, filed on Jul. 28, 2009, which is a continuation of application No. 12/082,488, filed on Apr. 10, 2008, now abandoned, which is a continuation of application No. 11/655,338, filed on Jan. 19, 2007, now abandoned.

(51) Int. Cl.
    C11D 3/42 (2006.01)
(52) U.S. Cl. ............ 510/392; 8/442; 524/82; 524/84; 524/601
(58) Field of Classification Search .......... 510/392; 8/442
    See application file for complete search history.

(56) References Cited

U.S. PATENT DOCUMENTS

| | | | |
|---|---|---|---|
| 2,220,099 A | 11/1940 | Guenther et al. |
| 2,477,383 A | 7/1949 | Lewis |
| 3,082,114 A | 3/1963 | Balli et al. |
| 3,172,723 A | 3/1965 | Hay et al. |
| 3,186,155 A | 6/1965 | Breen et al. |
| 3,215,486 A | 11/1965 | Hada et al. |
| 3,415,904 A | 12/1968 | Taniguchi et al. |
| 3,584,991 A | 6/1971 | Sturkey |
| 3,629,241 A | 12/1971 | Krause et al. |
| 3,748,093 A | 7/1973 | Gangwisch et al. |
| 3,758,335 A | 9/1973 | Bergman et al. |
| 3,929,678 A | 12/1975 | Laughman et al. |
| 3,958,928 A | 5/1976 | Lala |
| 3,961,880 A | 6/1976 | Reinert et al. |
| 3,986,972 A | 10/1976 | Loffelman et al. |
| 4,137,243 A | 1/1979 | Farmer et al. |
| 4,197,087 A | 4/1980 | Ami et al. |
| 4,217,105 A | 8/1980 | Goodman |
| 4,239,660 A | 12/1980 | Kingry |
| 4,260,529 A | 4/1981 | Letton |
| 4,264,495 A | 4/1981 | Maher et al. |
| 4,270,236 A | 6/1981 | Zurbuchen et al. |
| 4,283,197 A | 8/1981 | Schurings et al. |
| 4,288,042 A | 9/1981 | Sendzimir |
| 4,298,490 A | 11/1981 | Lange et al. |
| 4,412,934 A | 11/1983 | Chung et al. |
| 4,430,243 A | 2/1984 | Bragg |
| 4,454,146 A | 6/1984 | Borovian |
| 4,460,374 A | 7/1984 | Abel et al. |
| 4,483,779 A | 11/1984 | Llenado |
| 4,483,780 A | 11/1984 | Llenado |
| 4,483,781 A | 11/1984 | Hartman |
| 4,494,957 A | 1/1985 | Niwa et al. |
| 4,507,407 A | 3/1985 | Kluger et al. |
| 4,565,647 A | 1/1986 | Llenado |
| 4,601,725 A | 7/1986 | Keller et al. |
| 4,602,916 A | 7/1986 | Wilson |
| 4,634,551 A | 1/1987 | Burns |
| 4,728,453 A | 3/1988 | Choy |
| 4,728,455 A | 3/1988 | Revek |
| 4,800,037 A | 1/1989 | Mazzola |
| 4,810,410 A | 3/1989 | Diakun et al. |

(Continued)

FOREIGN PATENT DOCUMENTS

DE 25 57 783 A1 7/1977
DE 4 224 039 A1 1/1993

(Continued)

OTHER PUBLICATIONS

Hallas Geounrey, et al., Dyes Derived from Aminothiophenes—Part 3. Application of some Disperse Dyes Derived from 2-Aminothiophenes to Hydrophobic Fibres, Dyes and Pigments, 1997, pp. 215-228, vol. 33, No. 3.

(Continued)

*Primary Examiner* — Mark Eashoo
*Assistant Examiner* — M. Reza Asdjodi
(74) *Attorney, Agent, or Firm* — Melissa G Krasovec

(57) ABSTRACT

This invention relates to novel whitening agents for cellulosic substrates. The whitening agents are comprised of at least two components: at least one chromophore component and at least one polymeric component. Suitable chromophore components generally fluoresce blue, red, violet, or purple color when exposed to ultraviolet light, or they may absorb light to reflect these same shades. The whitening agents are further characterized by having a dispersion component value of the Hansen Solubility Parameter of less than or equal to about 17 $MPa^{0.5}$. This invention also relates to laundry care compositions including but not limited to liquid and/or powder laundry detergent formulations and rinse added fabric softening (RAFS) compositions that comprise such whitening agents.

9 Claims, 1 Drawing Sheet

U.S. PATENT DOCUMENTS

| | | | |
|---|---|---|---|
| 4,871,371 A | 10/1989 | Harris |
| 4,886,517 A | 12/1989 | Bugaut et al. |
| 4,912,203 A | 3/1990 | Kluger et al. |
| 4,915,854 A | 4/1990 | Mao et al. |
| 4,966,723 A | 10/1990 | Hodge et al. |
| 4,992,204 A | 2/1991 | Kluger et al. |
| 5,004,558 A | 4/1991 | Dyroff et al. |
| 5,039,782 A | 8/1991 | Langer et al. |
| 5,049,311 A | 9/1991 | Rasheed et al. |
| 5,059,244 A | 10/1991 | King et al. |
| 5,082,578 A | 1/1992 | Langer et al. |
| 5,114,606 A | 5/1992 | Van Vliet et al. |
| 5,114,611 A | 5/1992 | Van Kralinger et al. |
| 5,130,045 A | 7/1992 | Mitchell et al. |
| 5,132,431 A | 7/1992 | Fuchs |
| 5,153,161 A | 10/1992 | Kerschner et al. |
| 5,164,100 A | 11/1992 | Langer et al. |
| 5,194,416 A | 3/1993 | Jureller et al. |
| 5,227,084 A | 7/1993 | Martens et al. |
| 5,244,594 A | 9/1993 | Favre et al. |
| 5,246,612 A | 9/1993 | Van Dijik et al. |
| 5,246,620 A | 9/1993 | Gethoffer et al. |
| 5,246,621 A | 9/1993 | Favre et al. |
| 5,256,779 A | 10/1993 | Kershner et al. |
| 5,274,147 A | 12/1993 | Kershner et al. |
| 5,279,757 A | 1/1994 | Gethoffer et al. |
| 5,280,117 A | 1/1994 | Kershner et al. |
| 5,284,944 A | 2/1994 | Madison et al. |
| 5,310,934 A | 5/1994 | Cavaloloti et al. |
| 5,332,528 A | 7/1994 | Pan |
| 5,346,588 A | 9/1994 | Sixta et al. |
| 5,360,569 A | 11/1994 | Madison et al. |
| 5,370,826 A | 12/1994 | Madison et al. |
| 5,405,413 A | 4/1995 | Willey et al. |
| 5,442,066 A | 8/1995 | Madison et al. |
| 5,460,747 A | 10/1995 | Gosselink et al. |
| 5,478,357 A | 12/1995 | Madison et al. |
| 5,482,515 A | 1/1996 | Madison et al. |
| 5,487,818 A | 1/1996 | Cavallotti et al. |
| 5,503,639 A | 4/1996 | Willey et al. |
| 5,523,434 A | 6/1996 | Burns |
| 5,550,256 A | 8/1996 | Madison et al. |
| 5,574,179 A | 11/1996 | Wahl et al. |
| 5,576,282 A | 11/1996 | Miracle et al. |
| 5,578,136 A | 11/1996 | Taylor et al. |
| 5,584,888 A | 12/1996 | Miracle et al. |
| 5,591,833 A | 1/1997 | Hines et al. |
| 5,595,967 A | 1/1997 | Miracle et al. |
| 5,597,936 A | 1/1997 | Perkins et al. |
| 5,641,739 A | 6/1997 | Kott et al. |
| 5,654,421 A | 8/1997 | Willey et al. |
| 5,686,014 A | 11/1997 | Baillely et al. |
| 5,686,015 A | 11/1997 | Willey et al. |
| 5,686,401 A | 11/1997 | Willey et al. |
| 5,695,679 A | 12/1997 | Christie et al. |
| 5,698,504 A | 12/1997 | Christie et al. |
| 5,703,030 A | 12/1997 | Perkins et al. |
| 5,714,452 A | 2/1998 | Brouwer |
| 5,718,614 A | 2/1998 | Armond et al. |
| 5,728,671 A | 3/1998 | Rohrbaugh et al. |
| 5,739,327 A | 4/1998 | Arbogast et al. |
| 5,741,437 A | 4/1998 | Arbogast et al. |
| 5,759,990 A | 6/1998 | Wahl et al. |
| 5,877,315 A | 3/1999 | Deline et al. |
| 5,916,481 A | 6/1999 | Willey |
| 5,948,153 A | 9/1999 | Ann et al. |
| 5,958,289 A | 9/1999 | Arbogast et al. |
| 5,998,350 A | 12/1999 | Burns |
| 6,004,922 A | 12/1999 | Watson |
| 6,008,181 A | 12/1999 | Cripe et al. |
| 6,017,464 A | 1/2000 | Deline |
| 6,020,303 A | 2/2000 | Cripe et al. |
| 6,022,844 A | 2/2000 | Baillely et al. |
| 6,060,443 A | 5/2000 | Cripe et al. |
| 6,063,750 A | 5/2000 | Loffler et al. |
| 6,093,856 A | 7/2000 | Cripe et al. |
| 6,133,216 A | 10/2000 | Loffler et al. |
| 6,136,769 A | 10/2000 | Asano et al. |
| 6,140,294 A | 10/2000 | Delroisse et al. |
| 6,150,322 A | 11/2000 | Singleton et al. |
| 6,150,494 A | 11/2000 | Wang et al. |
| 6,153,577 A | 11/2000 | Cripe et al. |
| 6,180,123 B1 | 1/2001 | Mondet |
| 6,214,963 B1 | 4/2001 | Noguchi et al. |
| 6,221,825 B1 | 4/2001 | Williams et al. |
| 6,225,464 B1 | 5/2001 | Hiler, II et al. |
| 6,287,580 B1 | 9/2001 | Gott et al. |
| 6,302,921 B1 | 10/2001 | Delroisse et al. |
| 6,306,812 B1 | 10/2001 | Perkins et al. |
| 6,326,348 B1 | 12/2001 | Vinson et al. |
| 6,482,994 B2 | 11/2002 | Scheper et al. |
| 6,494,920 B1 | 12/2002 | Weuthen et al. |
| 6,521,581 B1 | 2/2003 | Hsu et al. |
| 6,616,711 B1 | 9/2003 | Känzig et al. |
| 6,723,846 B1 | 4/2004 | Metzger et al. |
| 6,875,811 B2 | 4/2005 | Danielson et al. |
| 7,208,459 B2 | 4/2007 | Sadlowski et al. |
| 7,235,518 B2 | 6/2007 | Brush et al. |
| 7,416,593 B2 | 8/2008 | Hasemann |
| 7,642,282 B2 | 1/2010 | Valenti et al. |
| 7,674,757 B2 | 3/2010 | Torres et al. |
| 2001/0031806 A1 | 10/2001 | Lutkenhorst et al. |
| 2002/0062763 A1 | 5/2002 | Macholdt et al. |
| 2002/0151235 A1 | 10/2002 | Bartl et al. |
| 2003/0082349 A1 | 5/2003 | Batlaw |
| 2003/0136701 A1 | 7/2003 | Giblin et al. |
| 2004/0204337 A1 | 10/2004 | Carona et al. |
| 2004/0229769 A1 | 11/2004 | Smith et al. |
| 2005/0235429 A1 | 10/2005 | Weber et al. |
| 2005/0288206 A1 | 12/2005 | Sadlowski et al. |
| 2005/0288207 A1 | 12/2005 | Sadlowski et al. |
| 2006/0019860 A1 | 1/2006 | Cardozo et al. |
| 2006/0079438 A1 | 4/2006 | Brush et al. |
| 2006/0183658 A1 | 8/2006 | Sadlowski et al. |
| 2006/0229224 A1 | 10/2006 | Batchelor |
| 2007/0203053 A1 | 8/2007 | Torres et al. |
| 2008/0034511 A1 | 2/2008 | Batchelor et al. |
| 2008/0096789 A1 | 4/2008 | Batchelor |
| 2008/0177089 A1 | 7/2008 | Sadlowski et al. |
| 2008/0235884 A1 | 10/2008 | Sadlowski et al. |
| 2009/0223003 A1 | 9/2009 | Batchelor et al. |
| 2009/0286709 A1 | 11/2009 | Sadlowski et al. |

FOREIGN PATENT DOCUMENTS

| | | |
|---|---|---|
| EP | 0 006 271 A1 | 1/1980 |
| EP | 0 133354 A1 | 2/1985 |
| EP | 537 381 A1 | 10/1991 |
| EP | 0 166 566 B1 | 10/1992 |
| EP | 544440 A2 | 6/1993 |
| EP | 544490 A1 | 6/1993 |
| EP | 549271 A1 | 6/1993 |
| EP | 549272 A1 | 6/1993 |
| EP | 0 790 244 A1 | 8/1997 |
| EP | 1 095 985 A1 | 5/2001 |
| GB | 1 419 125 A | 12/1975 |
| JP | 01 180816 A2 | 7/1989 |
| WO | WO 92/06162 A1 | 4/1992 |
| WO | WO 93/19038 A1 | 9/1993 |
| WO | WO 93/19146 A1 | 9/1993 |
| WO | WO 94/09099 A1 | 4/1994 |
| WO | WO 94/28102 A1 | 12/1994 |
| WO | WO 94/28104 A1 | 12/1994 |
| WO | WO 95/13351 A1 | 5/1995 |
| WO | WO 95/13352 A1 | 5/1995 |
| WO | WO 95/13353 A1 | 5/1995 |
| WO | WO 96/40661 A1 | 12/1996 |
| WO | WO 97/26315 A1 | 7/1997 |
| WO | WO 98/35002 A1 | 8/1998 |
| WO | WO 98/35003 A1 | 8/1998 |
| WO | WO 98/35004 A1 | 8/1998 |
| WO | WO 98/35005 A1 | 8/1998 |
| WO | WO 98/35006 A1 | 8/1998 |
| WO | WO 99/05082 A1 | 2/1999 |
| WO | WO 99/05084 A1 | 2/1999 |
| WO | WO 99/05241 A1 | 2/1999 |
| WO | WO 99/05242 A1 | 2/1999 |
| WO | WO 99/05243 A1 | 2/1999 |

| | | |
|---|---|---|
| WO | WO 99/05244 A1 | 2/1999 |
| WO | WO 99/07656 A2 | 2/1999 |
| WO | WO 99/14296 A1 | 3/1999 |
| WO | WO 00/23548 A1 | 4/2000 |
| WO | WO 00/23549 A1 | 4/2000 |
| WO | WO 00/32601 A2 | 6/2000 |
| WO | WO 00/47708 A1 | 8/2000 |
| WO | WO 01/42408 A2 | 6/2001 |
| WO | WO 2006/021285 A1 | 3/2006 |
| WO | WO 2006/027086 A1 | 3/2006 |

OTHER PUBLICATIONS

Harold, Richard W., Objective Instrumental Shade Sorting, Color Technology in the Textile Industry, Edited by Gultekin Celikiz and Rolf G. Kuehni, pp. 155-161.

Hansen, Charles M., Solubility Parameters—An Introduction, Hansen Solubility Parameters, A User's Handbook, CRC Press, 2000, pp. 1-23.

Kirk Othmer's Encyclopedia of Chemical Technology, 4$^{th}$ Ed (1992, John Wiley & Sons), vol. 4, pp. 271-300 Bleaching Agents (Survey).

Kirk Othmer, Encyclopedia of Chemical Technology, vol. 17, John Wiley and Sons, 1982 at pp. 27-90 and pp. 63-72.

M. L. Tobe, Base Hydrolysis of Transition-Metal Complexes, Adv. Igorg. Bioinorg. Mech. (1983), 2, pp. 1-94.

J. Chem Ed. (1989), 66 (12), 1043-45; The Synthesis and Characterization of Inorganic Compounds, W. L. Jolly (Prentice-Hall; 1970), pp. 461-463.

Inorg. Chem. 18, 1497-1502 (1979).

Inorg. Chem 21, 2881-2885 (1982).

Inorg. Chem, 18, 2023-2025 ( 1979).

Inorg. Synthesis, 173-176 (1960).

Journal of Physical Chemistry, 56, 22-25 (1952).

Rolf Griesser, Ciba-Geigy Ltd. "Whitenss and Tint", Jun. 1993.

(Liu Jun-na, Chen Zhi-rongb , and Yuan Shen-feng, Journal of Zhejiang university Science, 6B(6), 2005, pp. 584-589).

International Search Report, mailed Feb. 18, 2008, 7 pages.

Simmons, Deena M., et al., Characterization of Six Textile Dyes as Fluorescent Stains for Flow Cytometry, The Journal of Histochemistry and Cytochemistry, 1990, pp. 41-49, vol. 38, No. 1.

Performance Fibers; Material Safety Data Sheet; Polyester Fiber and Resin; MSDS No. PF0002; Current Issue Date: Nov. 2009; 6 pages.

Technical Bulletin/ Printed Circuit Board Film; Physical Properties of Polyester Film Base; High Complexity PCB Starts With the Right Phototools; Mar. 2010; Kodak Publication No. TI-2598; Eastman Kodak Company; Rochester, NY.

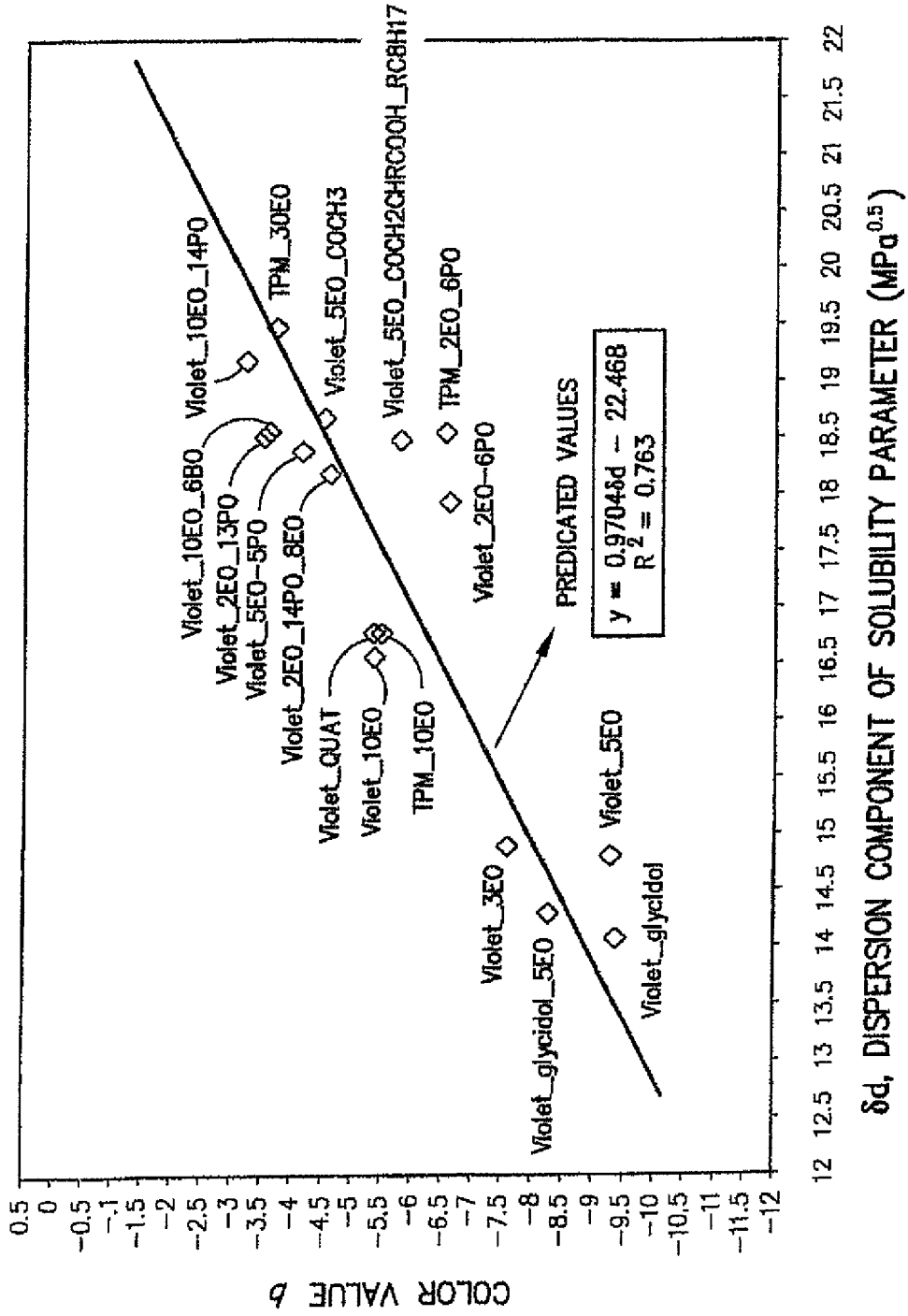

WHITENING AGENTS FOR CELLULOSIC SUBTRATES

CROSS REFERENCE TO RELATED APPLICATIONS

This application is a continuation of and claims priority under 35 U.S.C. §120 to U.S. application Ser. No. 12/510,327, filed Jul. 28, 2009 which in turn is a continuation of U.S. application Ser. No. 12/082,488, filed Apr. 10, 2008 now abandoned, which in turn is a continuation of and claims priority under 35 U.S.C. §120 to U.S. application Ser. No. 11/655,338, filed Jan. 19, 2007 now abandoned.

TECHNICAL FIELD

This invention relates to novel whitening agents for cellulosic substrates. The whitening agents are comprised of at least two components: at least one chromophore component and at least one polymeric component. Suitable chromophore components generally fluoresce blue, red, violet, or purple color when exposed to ultraviolet light, or they may absorb light to reflect these same shades. The whitening agents are further characterized by having a dispersion component value of the Hansen Solubility Parameter of less than or equal to about 17 $MPa^{0.5}$. These whitening agents may be ideal for use in laundry care compositions including but not limited to liquid and/or powder laundry detergent formulations and rinse added fabric softening (RAFS) compositions.

BACKGROUND

The use of whitening agents, either optical brighteners or blueing agents, in textile applications is well known in the prior art. As textile substrates age, their color tends to fade or yellow due to exposure to light, air, soil, and natural degradation of the fibers that comprise the substrates. Thus, the purpose of whitening agents is generally to visually brighten these textile substrates and counteract the fading and yellowing of the substrates. Typically, whitening agents may be found in laundry detergents, fabric softeners, or rinse aids and are therefore applied to textile substrates during the laundering process. However, it is important that whitening agents function to brighten treated textile substrates without causing undesirable staining of the textile substrates.

Cellulosic substrates, in particular, tend to exhibit a yellow hue after exposure to light, air, and/or soiling. This yellowness is often difficult to reverse by normal laundering procedures. As a result, there exists a need for improved whitening agents which are capable of eliminating the yellowness exhibited by ageing cellulosic substrates. By utilizing such improved whitening agents, the life of the textile substrates, such as clothing articles, table linens, etc., may be extended.

The present invention offers advantages over U.S. Pat. Nos. 4,137,243, 5,039,782 and US Patent Application Publication No. 2005/0288206 as this invention takes advantage of compounds having a Hansen Solubility Parameter of less than or equal to about 17 $MPa^{0.5}$ and which emit light with wavelengths in the range of blue, red, violet, purple, or combinations thereof upon exposure to ultraviolet light (or, they absorb light to produce the same shades) in order to neutralize the yellowness of cellulosic substrates. These compounds function ideally as whitening agents for cellulosic substrates and may be incorporated into laundry detergent formulations for use by consumers during the laundering process.

SUMMARY OF INVENTION

This invention relates to novel whitening agents for cellulosic substrates. The whitening agents are comprised of at least two components: at least one chromophore component and at least one polymeric component. Suitable chromophore components generally fluoresce blue, red, violet, or purple color when exposed to ultraviolet light, or they may absorb light to reflect these same shades. The whitening agents are further characterized by having a dispersion component value of the Hansen Solubility Parameter of less than or equal to about 17 $MPa^{0.5}$. This invention also relates to laundry care compositions including but not limited to liquid and/or powder laundry detergent formulations and rinse added fabric softening (RAFS) compositions that comprise such whitening agents.

BRIEF DESCRIPTION OF THE DRAWINGS

FIG. 1 is a graphical representation of dispersion component values of the Hansen Solubility Parameter versus CIELab b* values for various whitening agents after 1 rinse cycle.

DETAILED DESCRIPTION

As used herein, "cellulosic substrates" are intended to include any substrate which comprises at least a majority by weight of cellulose. Cellulose may be found in wood, cotton, linen, jute, and hemp. Cellulosic substrates may be in the form of powders, fibers, pulp and articles formed from powders, fibers and pulp. Cellulosic fibers, include, without limitation, cotton, rayon (regenerated cellulose), acetate (cellulose acetate), triacetate (cellulose triacetate), and mixtures thereof. Articles formed from cellulosic fibers include textile articles such as fabrics. Articles formed from pulp include paper.

As used herein, the term "laundry care composition" includes, unless otherwise indicated, granular, powder, liquid, gel, paste, bar form and/or flake type washing agents and/or fabric treatment compositions.

As used herein, the term "fabric treatment composition" includes, unless otherwise indicated, fabric softening compositions, fabric enhancing compositions, fabric freshening compositions and combinations there of. Such compositions may be, but need not be rinse added compositions.

As used herein, the articles including "the", "a" and "an" when used in a claim, are understood to mean one or more of what is claimed or described.

As used herein, the terms "include", "includes" and "including" are meant to be non-limiting.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited are, in relevant part, incorporated herein by reference; the citation of any document is not to be construed as an admission that it is prior art with respect to the present invention.

The whitening agents of the present invention may be dyes, pigments, or polymeric colorants comprising a chromophore constituent and a polymeric constituent. The chromophore constituent is characterized in that it emits or absorbs wavelength in the range of blue, red, violet, purple, or combinations thereof upon exposure to light. Preferably, the chromophore constituent exhibits an absorbance spectrum value from about 520 nanometers to about 640 nanometers in water, and more preferably from about 570 nanometers to about 610 nanometers in water. Preferably, the chromophore constituent exhibits an emission spectrum value from about 400 nanometers to about 480 nanometers in water.

Examples of suitable polymeric constituents include polyoxyalkylene chains having multiple repeating units. Preferably the polymeric constituents include polyoxyalkylene chains having from 2 to about 20 repeating units, and more preferably from 2 to about 10 or even from about 4 to about 6 repeating units. Non-limiting examples of polyoxyalkylene chains include ethylene oxide, propylene oxide, glycidol oxide, butylene oxide and mixtures thereof.

The whitening agent of the present invention may be characterized by the following structure:

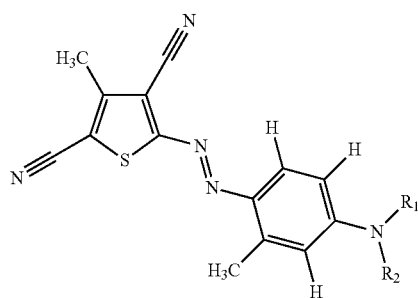

Wherein $R_1$ and $R_2$ can independently be selected from:
a) $[(CH_2CR'HO)_x(CH_2CR''HO)_yH]$
   wherein R' is selected from the group consisting of H, $CH_3$, $CH_2$—O—$(CH_2CH_2O)_zH$, and mixtures thereof; wherein R" is selected from the group consisting of H, $CH_2$—O—$(CH_2CH_2O)_zH$, and mixtures thereof; wherein x+y≦5; wherein y≧1; and wherein z=0 to 5;
b) $R_1$=alkyl, aryl or aryl alkyl and $R_2$=$[(CH_2CR'HO)_x(CH_2CR''HO)_yH]$
   wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein x+y≦10; wherein y≧1; and wherein z=0 to 5;
c) $R_1$=$[CH_2CH_2(OR_3)CH_2OR_4]$ and $R_2$=$[CH_2CH_2(OR_3)CH_2OR_4]$
   wherein $R_3$ is selected from the group consisting of H, $(CH_2CH_2O)_zH$, and mixtures thereof; and wherein z=0 to 10;
   wherein $R_4$ is selected from the group consisting of ($C_1$-$C_{16}$)alkyl, aryl groups, and mixtures thereof; and
d) wherein R1 and R2 can independently be selected from the amino addition product of styrene oxide, glycidyl methyl ether, isobutyl glycidyl ether, isopropylglycidyl ether, t-butyl glycidyl ether, 2-ethylhexylgycidyl ether, and glycidylhexadecyl ether, followed by the addition of from 1 to 10 alkylene oxide units.

A preferred whitening agent of the present invention may be characterized by the following structure:

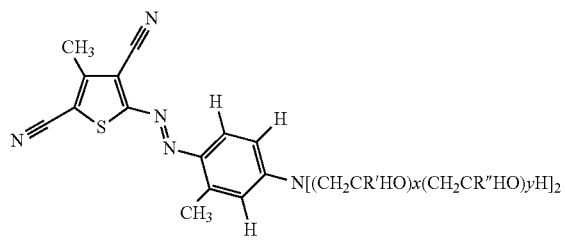

wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein x+y≦5; wherein y≧1; and wherein z=0 to 5.

Another characteristic of the whitening agent of the present invention is its affinity for cellulosic material. Affinity may be determined quantitatively from using the dispersion force component of the Hansen Solubility Parameter. The Hansen Solubility Parameter is a three component measuring system that includes a dispersion force component ($\delta_d$), a hydrogen bonding component ($\delta_h$), and a polar component ($\delta_p$). The Hansen Solubility Parameter "$\delta$" is derived from the fact that the total cohesive energy, which is the energy required to break all the cohesive bonds, is the combination of the dispersion forces (d), the molecular dipole forces (p), and the hydrogen bonding forces (h) according to the following equation:

$$\delta^2 = \delta_d^2 + \delta_p^2 + \delta_h^2. \quad (1)$$

Dispersion forces are weak attractive forces between non-polar molecules. The magnitude of these forces depends on the polarizability of the molecule, and the dispersion Hansen Solubility Parameter, $\delta_d$, typically increases with increasing volume (and size) of the molecule, all other properties being roughly equal. The parameter "$\delta_p$" increases with increasing polarity of the molecule.

Hansen Solubility Parameters are calculated at 25° C. with ChemSW's Molecular Modeling Pro v.6.1.9 software package which uses an unpublished proprietary algorithm that is based on values published in the Handbook of Solubility Parameters and Other Parameters by Allan F. M. Barton (CRC Press, 1983) for solvents obtained experimentally by Hansen. All values of the Hansen Solubility Parameter reported herein are in units of $MPa^{0.5}$ (square root of megaPascals). Hansen originally determined the solubility parameter of solvents for polymer solutions. While Hansen Solubility Parameter calculation has been applied successfully to a wide range of applications such as solubility of biological materials, characterization of pigments, fillers and fibers, etc., it has not heretofore been adapted to polymeric colorants.

Thus, for the effective whitening agents of the present invention, it is preferable that the dispersion force component of the Hansen Solubility Parameter, $\delta_d$, is less than or equal to about 17, and more preferably less than or equal to about 15. It may also be desirable that the dispersion force component of the Hansen Solubility Parameter is from about 12 to about 17, and more preferably from about 12 to about 15.

While the affinity of the whitening agent to the cellulosic material appears to correlate very well with the Hansen Solubility Dispersion Component parameter, the invention is not limited to the use of $\delta_d$. Other molecular descriptors, which are directly or indirectly related to $\delta_d$ such as, for example, polarizability, radius of gyration, molecular volume, and Jurs descriptors based on partial atomic charges mapped on solvent-accessible surface area, were also considered.

However, the goodness of fit of the univariate correlations of the affinity with these descriptors was not as good as with $\delta_d$.

Without being bound by theory, it is believed that the affinity of the whitening agents for the cellulose substrates may be ascribed to Van der Waals forces, the attractive forces that exist between electrically neutral molecules in close proximity to one another. It is also postulated that if the cellulose substrate is comprised of porous regions, the whitening agent, or portions thereof, may be physically trapped in the pores of the cellulose, depending on the size of the molecule as compared to the diameter of the pores. This physical entrapment may provide some level of durability to protect the whitening agent from being easily removed form the cellulose substrate upon exposure to washing or rinsing.

The whitening agent's described in the present specification may be incorporated into a laundry care composition including but not limited to laundry detergents and fabric care compositions. Such compositions comprise one or more of said whitening agents and a laundry care ingredient. The whitening agent may be added to cellulose substrates using a variety of application techniques. For application to cellulose-containing textile substrates, the whitening agent is preferably included as an additive in laundry detergent. Thus, application to the cellulose-containing textile substrate actually occurs when a consumer adds laundry detergent to a washing machine. Similarly, RAFS compositions are typically added in the rinse cycle, which is after the detergent solution has been used and replaced with the rinsing solution in typical laundering processes. For application to cellulosic paper substrates, the whitening agent may be added to the paper pulp mixture prior to formation of the final paper product.

The laundry care compositions including laundry detergents may be in solid or liquid form, including a gel form. The laundry detergent composition comprises a surfactant in an amount sufficient to provide desired cleaning properties.

The whitening agent may be present in the laundry detergent composition in an amount from about 0.0001% to about 10% by weight of the composition, more preferably from about 0.0001% to about 5% by weight of the composition, and even more preferably from about 0.0001% to about 1% by weight of the composition.

The laundry detergent composition comprises a surfactant in an amount sufficient to provide desired cleaning properties. In one embodiment, the laundry detergent composition comprises, by weight, from about 5% to about 90% of the surfactant, and more specifically from about 5% to about 70% of the surfactant, and even more specifically from about 5% to about 40%. The surfactant may comprise anionic, nonionic, cationic, zwitterionic and/or amphoteric surfactants. In a more specific embodiment, the detergent composition comprises anionic surfactant, nonionic surfactant, or mixtures thereof.

Suitable anionic surfactants useful herein can comprise any of the conventional anionic surfactant types typically used in liquid detergent products. These include the alkyl benzene sulfonic acids and their salts as well as alkoxylated or non-alkoxylated alkyl sulfate materials.

Exemplary anionic surfactants are the alkali metal salts of C.sub.10-16 alkyl benzene sulfonic acids, preferably C.sub.11-14 alkyl benzene sulfonic acids. Preferably the alkyl group is linear and such linear alkyl benzene sulfonates are known as "LAS". Alkyl benzene sulfonates, and particularly LAS, are well known in the art. Such surfactants and their preparation are described for example in U.S. Pat. Nos. 2,220,099 and 2,477,383. Especially preferred are the sodium and potassium linear straight chain alkylbenzene sulfonates in which the average number of carbon atoms in the alkyl group is from about 11 to 14. Sodium $C_{11}$-$C_{14}$, e.g., $C_{12}$, LAS is a specific example of such surfactants.

Another exemplary type of anionic surfactant comprises ethoxylated alkyl sulfate surfactants. Such materials, also known as alkyl ether sulfates or alkyl polyethoxylate sulfates, are those which correspond to the formula: R'—O—$(C_2H_4O)_n$—$SO_3M$ wherein R' is a $C_8$-$C_{20}$ alkyl group, n is from about 1 to 20, and M is a salt-forming cation. In a specific embodiment, R' is $C_{10}$-$C_{18}$ alkyl, n is from about 1 to 15, and M is sodium, potassium, ammonium, alkylammonium, or alkanolammonium. In more specific embodiments, R' is a $C_{12}$-$C_{16}$, n is from about 1 to 6 and M is sodium.

The alkyl ether sulfates will generally be used in the form of mixtures comprising varying R' chain lengths and varying degrees of ethoxylation. Frequently such mixtures will inevitably also contain some non-ethoxylated alkyl sulfate materials, i.e., surfactants of the above ethoxylated alkyl sulfate formula wherein n=0. Non-ethoxylated alkyl sulfates may also be added separately to the compositions of this invention and used as or in any anionic surfactant component which may be present. Specific examples of non-alkoxylated, e.g., non-ethoxylated, alkyl ether sulfate surfactants are those produced by the sulfation of higher $C_8$-$C_{20}$ fatty alcohols. Conventional primary alkyl sulfate surfactants have the general formula: $ROSO_3$-$M^+$ wherein R is typically a linear $C_8$-$C_{20}$ hydrocarbyl group, which may be straight chain or branched chain, and M is a water-solubilizing cation. In specific embodiments, R is a $C_{10}$-$C_{15}$ alkyl, and M is alkali metal, more specifically R is $C_{12}$-$C_{14}$ and M is sodium.

Specific, non-limiting examples of anionic surfactants useful herein include: a) $C_{11}$-$C_{18}$ alkyl benzene sulfonates (LAS); b) $C_{10}$-$C_{20}$ primary, branched-chain and random alkyl sulfates (AS); c) $C_{10}$-$C_{18}$ secondary (2,3) alkyl sulfates having formulae (I) and (II): wherein M in formulae (I) and (II) is hydrogen or a cation which provides charge neutrality, and all M units, whether associated with a surfactant or adjunct ingredient, can either be a hydrogen atom or a cation depending upon the form isolated by the artisan or the relative pH of the system wherein the compound is used, with non-limiting examples of preferred cations including sodium, potassium, ammonium, and mixtures thereof, and x is an integer of at least about 7, preferably at least about 9, and y is an integer of at least 8, preferably at least about 9; d) $C_{10}$-$C_{18}$ alkyl alkoxy sulfates (AE.sub.xS) wherein preferably x is from 1-30; e) $C_{10}$-$C_{18}$ alkyl alkoxy carboxylates preferably comprising 1-5 ethoxy units; f) mid-chain branched alkyl sulfates as discussed in U.S. Pat. No. 6,020,303 and U.S. Pat. No. 6,060,443; g) mid-chain branched alkyl alkoxy sulfates as discussed in U.S. Pat. No. 6,008,181 and U.S. Pat. No. 6,020,303; h) modified alkylbenzene sulfonate (MLAS) as discussed in WO 99/05243, WO 99/05242, WO 99/05244, WO 99/05082, WO 99/05084, WO 99/05241, WO 99/07656, WO 00/23549, and WO 00/23548; i) methyl ester sulfonate (MES); and j) alpha-olefin sulfonate (AOS).

Suitable nonionic surfactants useful herein can comprise any of the conventional nonionic surfactant types typically used in liquid detergent products. These include alkoxylated fatty alcohols and amine oxide surfactants. Preferred for use in the liquid detergent products herein are those nonionic surfactants which are normally liquid.

Suitable nonionic surfactants for use herein include the alcohol alkoxylate nonionic surfactants. Alcohol alkoxylates are materials which correspond to the general formula: $R^1(C_mH_{2m}O)_nOH$ wherein $R^1$ is a $C_8$-$C_{16}$ alkyl group, m is from 2 to 4, and n ranges from about 2 to 12. Preferably $R^1$ is an alkyl group, which may be primary or secondary, that comprises from about 9 to 15 carbon atoms, more preferably from about 10 to 14 carbon atoms. In one embodiment, the alkoxylated fatty alcohols will also be ethoxylated materials that contain from about 2 to 12 ethylene oxide moieties per molecule, more preferably from about 3 to 10 ethylene oxide moieties per molecule.

The alkoxylated fatty alcohol materials useful in the liquid detergent compositions herein will frequently have a hydrophilic-lipophilic balance (HLB) which ranges from about 3 to 17. More preferably, the HLB of this material will range from about 6 to 15, most preferably from about 8 to 15. Alkoxylated fatty alcohol nonionic surfactants have been marketed under the tradenames Neodol and Dobanol by the Shell Chemical Company.

Another suitable type of nonionic surfactant useful herein comprises the amine oxide surfactants. Amine oxides are materials which are often referred to in the art as "semi-polar" nonionics. Amine oxides have the formula: $R(EO)_x(PO)_y(BO)_zN(O)(CH_2R')_2 \cdot qH_2O$. In this formula, R is a relatively long-chain hydrocarbyl moiety which can be saturated or unsaturated, linear or branched, and can contain from 8 to 20, preferably from 10 to 16 carbon atoms, and is more preferably $C_{12}$-$C_{16}$ primary alkyl. R' is a short-chain moiety, preferably selected from hydrogen, methyl and —$CH_2OH$. When x+y+z is different from 0, EO is ethyleneoxy, PO is propyleneneoxy and BO is butyleneoxy. Amine oxide surfactants are illustrated by $C_{12-14}$ alkyldimethyl amine oxide.

Non-limiting examples of nonionic surfactants include: a) $C_{12}$-$C_{18}$ alkyl ethoxylates, such as, NEODOL® nonionic surfactants from Shell; b) $C_6$-$C_{12}$ alkyl phenol alkoxylates wherein the alkoxylate units are a mixture of ethyleneoxy and propyleneoxy units; c) $C_{12}$-$C_{18}$ alcohol and $C_6$-$C_{12}$ alkyl phenol condensates with ethylene oxide/propylene oxide block polymers such as Pluronic® from BASF; d) $C_{14}$-$C_{22}$ midchain branched alcohols, BA, as discussed in U.S. Pat. No. 6,150,322; e) $C_{14}$-$C_{22}$ mid-chain branched alkyl alkoxylates, $BAE_x$, wherein x if from 1-30, as discussed in U.S. Pat. No. 6,153,577, U.S. Pat. No. 6,020,303 and U.S. Pat. No. 6,093,856; f) Alkylpolysaccharides as discussed in U.S. Pat. No. 4,565,647 to Llenado, issued Jan. 26, 1986; specifically alkylpolyglycosides as discussed in U.S. Pat. No. 4,483,780 and U.S. Pat. No. 4,483,779; g) Polyhydroxy fatty acid amides as discussed in U.S. Pat. No. 5,332,528, WO 92/06162, WO 93/19146, WO 93/19038, and WO 94/09099; and h) ether capped poly(oxyalkylated) alcohol surfactants as discussed in U.S. Pat. No. 6,482,994 and WO 01/42408.

In the laundry detergent compositions herein, the detersive surfactant component may comprise combinations of anionic and nonionic surfactant materials. When this is the case, the weight ratio of anionic to nonionic will typically range from 10:90 to 90:10, more typically from 30:70 to 70:30.

Cationic surfactants are well known in the art and non-limiting examples of these include quaternary ammonium surfactants, which can have up to 26 carbon atoms. Additional examples include a) alkoxylate quaternary ammonium (AQA) surfactants as discussed in U.S. Pat. No. 6,136,769; b) dimethyl hydroxyethyl quaternary ammonium as discussed in U.S. Pat. No. 6,004,922; c) polyamine cationic surfactants as discussed in WO 98/35002, WO 98/35003, WO 98/35004, WO 98/35005, and WO 98/35006; d) cationic ester surfactants as discussed in U.S. Pat. Nos. 4,228,042, 4,239,660 4,260,529 and U.S. Pat. No. 6,022,844; and e) amino surfactants as discussed in U.S. Pat. No. 6,221,825 and WO 00/47708, specifically amido propyldimethyl amine (APA).

Non-limiting examples of zwitterionic surfactants include derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48, for examples of zwitterionic surfactants; betaine, including alkyl dimethyl betaine and cocodimethyl amidopropyl betaine, $C_8$ to $C_{18}$ (preferably $C_{12}$ to $C_{18}$) amine oxides and sulfo and hydroxy betaines, such as N-alkyl-N,N-dimethylammino-1-propane sulfonate where the alkyl group can be $C_8$ to $C_{18}$, preferably $C_{10}$ to $C_{14}$.

Non-limiting examples of ampholytic surfactants include aliphatic derivatives of secondary or tertiary amines, or aliphatic derivatives of heterocyclic secondary and tertiary amines in which the aliphatic radical can be straight- or branched-chain. One of the aliphatic substituents comprises at least about 8 carbon atoms, typically from about 8 to about 18 carbon atoms, and at least one comprises an anionic water-solubilizing group, e.g. carboxy, sulfonate, sulfate. See U.S. Pat. No. 3,929,678 to Laughlin et al., issued Dec. 30, 1975 at column 19, lines 18-35, for examples of ampholytic surfactants.

As noted, the compositions may be in the form of a solid, either in tablet or particulate form, including, but not limited to particles, flakes, or the like, or the compositions may be in the form of a liquid. The liquid detergent compositions comprise an aqueous, non-surface active liquid carrier. Generally, the amount of the aqueous, non-surface active liquid carrier employed in the compositions herein will be effective to solubilize, suspend or disperse the composition components. For example, the compositions may comprise, by weight, from about 5% to about 90%, more specifically from about 10% to about 70%, and even more specifically from about 20% to about 70% of the aqueous, non-surface active liquid carrier.

The most cost effective type of aqueous, non-surface active liquid carrier is, of course, water itself. Accordingly, the aqueous, non-surface active liquid carrier component will generally be mostly, if not completely, comprised of water. While other types of water-miscible liquids, such alkanols, diols, other polyols, ethers, amines, and the like, have been conventionally been added to liquid detergent compositions as co-solvents or stabilizers, for purposes of the present invention, the utilization of such water-miscible liquids should be minimized to hold down composition cost. Accordingly, the aqueous liquid carrier component of the liquid detergent products herein will generally comprise water present in concentrations ranging from about 5% to about 90%, more preferably from about 20% to about 70%, by weight of the composition.

Detergent compositions may also contain bleaching agents. Suitable bleaching agents include, for example, hydrogen peroxide sources, such as those described in detail in the herein incorporated Kirk Othmer's Encyclopedia of Chemical Technology, 4th Ed (1992, John Wiley & Sons), Vol. 4, pp. 271-300 "Bleaching Agents (Survey)." These hydrogen peroxide sources include the various forms of sodium perborate and sodium percarbonate, including various coated and modified forms of these compounds.

The preferred source of hydrogen peroxide used herein can be any convenient source, including hydrogen peroxide itself.

For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Also useful are sources of available oxygen such as persulfate bleach (e.g., OXONE, manufactured by DuPont). Sodium perborate monohydrate and sodium percarbonate are particularly preferred. Mixtures of any convenient hydrogen peroxide sources can also be used.

A suitable percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with a silicate, borate or water-soluble surfactants. Percarbonate is available from various commercial sources such as FMC, Solvay and Tokai Denka.

Compositions of the present invention may also comprise as the bleaching agent a chlorine-type bleaching material. Such agents are well known in the art, and include for example sodium dichloroisocyanurate ("NaDCC"). However, chlorine-type bleaches are less preferred for compositions which comprise enzymes.

(a) Bleach Activators

Preferably, the peroxygen bleach component in the composition is formulated with an activator (peracid precursor). The activator is present at levels of from about 0.01%, preferably from about 0.5%, more preferably from about 1% to about 15%, preferably to about 10%, more preferably to about 8%, by weight of the composition. A bleach activator as used herein is any compound which, when used in conjunction with a hydrogen peroxide, source leads to the in situ production of the peracid corresponding to the bleach activator. Various non-limiting examples of activators are disclosed in U.S. Pat. Nos. 5,576,282; 4,915,854 and 4,412,934. See also U.S. Pat. No. 4,634,551 for other typical bleaches and activators useful herein.

Preferred activators are selected from the group consisting of tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzenesulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters and mixtures thereof, most preferably benzoylcaprolactam and benzoylvalerolactam. Particularly preferred bleach activators in the pH range from about 8 to about 11 are those selected having an OBS or VL leaving group. Preferred hydrophobic bleach activators include, but are not limited to, nonanoyloxybenzene-sulphonate (NOBS); 4-[N-(nonanoyl)amino hexanoyloxy]-benzene sulfonate sodium salt (NACA-OBS), an example of which is described in U.S. Pat. No. 5,523,434; dodecanoyloxybenzenesulphonate (LOBS or $C_{12}$-OBS); 10-undecenoyloxybenzenesulfonate (UDOBS or $C_{11}$-OBS with unsaturation in the 10 position); and decanoyloxybenzoic acid (DOBA).

Preferred bleach activators are those described in U.S. Pat. No. 5,998,350 to Burns et al.; U.S. Pat. No. 5,698,504 to Christie et al.; U.S. Pat. No. 5,695,679 to Christie et al.; U.S. Pat. No. 5,686,401 to Willey et al.; U.S. Pat. No. 5,686,014 to Hartshorn et al.; U.S. Pat. No. 5,405,412 to Willey et al.; U.S. Pat. No. 5,405,413 to Willey et al.; U.S. Pat. No. 5,130,045 to Mitchel et al.; and U.S. Pat. No. 4,412,934 to Chung et al., and copending patent application Ser. No. 08/064,564, all of which are incorporated herein by reference.

The mole ratio of peroxygen source (as AvO) to bleach activator in the present invention generally ranges from at least 1:1, preferably from about 20:1, more preferably from about 10:1 to about 1:1, preferably to about 3:1.

Quaternary substituted bleach activators may also be included. The present laundry compositions preferably comprise a quaternary substituted bleach activator (QSBA) or a quaternary substituted peracid (QSP, preferably a quaternary substituted percarboxylic acid or a quaternary substituted peroxyimidic acid); more preferably, the former. Preferred QSBA structures are further described in U.S. Pat. No. 5,686,015 to Willey et al.; U.S. Pat. No. 5,654,421 to Taylor et al.; U.S. Pat. No. 5,460,747 to Gosselink et al.; U.S. Pat. No. 5,584,888 to Miracle et al.; U.S. Pat. No. 5,578,136 to Taylor et al.; all of which are incorporated herein by reference.

Highly preferred bleach activators useful herein are amide-substituted as described in U.S. Pat. Nos. 5,698,504; 5,695,679; and 5,686,014, each of which are cited herein above. Preferred examples of such bleach activators include: (6-octanamidocaproyl) oxybenzenesulfonate, (6-nonanamidocaproyl)oxybenzenesulfonate, (6-decanamidocaproyl) oxybenzenesulfonate and mixtures thereof.

Other useful activators are disclosed in U.S. Pat. Nos. 5,698,504; 5,695,679; and 5,686,014, each of which is cited herein above, and in U.S. Pat. No. 4,966,723 to Hodge et al. These activators include benzoxazin-type activators, such as a $C_6H_4$ ring to which is fused in the 1,2-positions a moiety —C(O)OC($R^1$)=N—.

Nitriles, such as acetonitriles and/or ammonium nitriles and other quaternary nitrogen containing nitriles, are another class of activators that are useful herein. Non-limiting examples of such nitrile bleach activators are described in U.S. Pat. Nos. 6,133,216; 3,986,972; 6,063,750; 6,017,464; 5,958,289; 5,877,315; 5,741,437; 5,739,327; 5,004,558; and in EP Nos. 790 244, 775 127, 1 017 773, 1 017 776; and in WO 99/14302, WO 99/14296, WO96/40661, all of which are incorporated herein by reference.

Depending on the activator and precise application, good bleaching results can be obtained from bleaching systems having an in-use pH of from about 6 to about 13, and preferably from about 9.0 to about 10.5. Typically, for example, activators with electron-withdrawing moieties are used for near-neutral or sub-neutral pH ranges. Alkalis and buffering agents can be used to secure such pH.

Acyl lactam activators, as described in U.S. Pat. Nos. 5,698,504; 5,695,679 and 5,686,014, each of which is cited herein above, are very useful herein, especially the acyl caprolactams (see for example WO 94-28102 A) and acyl valerolactams (see U.S. Pat. No. 5,503,639 to Willey et al. incorporated herein by reference).

(b) Organic Peroxides, especially Diacyl Peroxides

These are extensively illustrated in Kirk Othmer, Encyclopedia of Chemical Technology, Vol. 17, John Wiley and Sons, 1982 at pages 27-90 and especially at pages 63-72, all incorporated herein by reference. If a diacyl peroxide is used, it will preferably be one which exerts minimal adverse impact on fabric care, including color care.

(c) Metal-Containing Bleach Catalysts

The compositions and methods of the present invention can also optionally include metal-containing bleach catalysts, preferably manganese and cobalt-containing bleach catalysts.

One type of metal-containing bleach catalyst is a catalyst system comprising a transition metal cation of defined bleach catalytic activity (such as copper, iron, titanium, ruthenium tungsten, molybdenum, or manganese cations), an auxiliary metal cation having little or no bleach catalytic activity (such as zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243 to Bragg.

Manganese Metal Complexes

If desired, the compositions herein can be catalyzed by means of a manganese compound. Such compounds and levels of use are well known in the art and include, for example, the manganese-based catalysts disclosed in U.S. Pat. Nos. 5,576,282; 5,246,621; 5,244,594; 5,194,416; and 5,114,606; and European Pat. App. Pub. Nos. 549,271 A1; 549,272 A1; 544,440 A2; and 544,490 A1. Preferred examples of these catalysts include $Mn^{IV}_2(u-O)_3(1,4,7\text{-trimethyl-1,4,7-triazacyclononane})_2(PF_6)_2$, $Mn^{III}_2(u-O)_1(u-OAc)_2(1,4,7\text{-trimethyl-1,4,7-triazacyclononane})_2(ClO_4)_2$, $Mn^{IV}_4(u-O)_6(1,4,7\text{-triazacyclononane})_4(ClO_4)_4$, $Mn^{III}Mn^{IV}_4(u-O)_1(u-OAc)_2(1,4,7\text{-trimethyl-1,4,7-triazacyclononane})_2(ClO_4)_3$, $Mn^{IV}(1,4,7\text{-trimethyl-1,4,7-triazacyclononane})-(OCH_3)_3(PF_6)$, and mixtures thereof. Other metal-based bleach catalysts include those disclosed in U.S. Pat. Nos. 4,430,243 and 5,114,611. The use of manganese with various complex ligands to enhance bleaching is also reported in the following: U.S. Pat. Nos. 4,728,455; 5,284,944; 5,246,612; 5,256,779; 5,280,117; 5,274,147; 5,153,161; and 5,227,084.

Cobalt Metal Complexes

Cobalt bleach catalysts useful herein are known, and are described, for example, in U.S. Pat. Nos. 5,597,936; 5,595, 967; and 5,703,030; and M. L. To be, "Base Hydrolysis of Transition-Metal Complexes", Adv. Inorg. Bioinorg. Mech., (1983), 2, pages 1-94. The most preferred cobalt catalyst useful herein are cobalt pentaamine acetate salts having the formula $[Co(NH_3)_5OAc]T_y$, wherein "OAc" represents an acetate moiety and "$T_y$" is an anion, and especially cobalt pentaamine acetate chloride, $[Co(NH_3)_5OAc]Cl_2$; as well as $[Co(NH_3)_5OAc](OAc)_2$; $[Co(NH_3)_5OAc](PF_6)_2$; $[Co(NH_3)_5OAc](SO_4)$; $[Co-(NH_3)_5OAc](BF_4)_2$; and $[Co(NH_3)_5OAc](NO_3)_2$ (herein "PAC").

These cobalt catalysts are readily prepared by known procedures, such as taught for example in U.S. Pat. Nos. 6,302, 921; 6,287,580; 6,140,294; 5,597,936; 5,595,967; and 5,703, 030; in the To be article and the references cited therein; and in U.S. Pat. No. 4,810,410; J. Chem. Ed. (1989), 66 (12), 1043-45; The Synthesis and Characterization of Inorganic Compounds, W. L. Jolly (Prentice-Hall; 1970), pp. 461-3; Inorg. Chem., 18, 1497-1502 (1979); Inorg. Chem., 21, 2881-2885 (1982); Inorg. Chem., 18, 2023-2025 (1979); Inorg. Synthesis, 173-176 (1960); and Journal of Physical Chemistry, 56, 22-25 (1952).

Transition Metal Complexes of Macropolycyclic Rigid Ligands

Compositions herein may also suitably include as bleach catalyst a transition metal complex of a macropolycyclic rigid ligand. The amount used is a catalytically effective amount, suitably about 1 ppb or more, for example up to about 99.9%, more typically about 0.001 ppm or more, preferably from about 0.05 ppm to about 500 ppm (wherein "ppb" denotes parts per billion by weight and "ppm" denotes parts per million by weight).

Transition-metal bleach catalysts of Macrocyclic Rigid Ligands which are suitable for use in the invention compositions can in general include known compounds where they conform with the definition herein, as well as, more preferably, any of a large number of novel compounds expressly designed for the present laundry or laundry uses, and are non-limitingly illustrated by any of the following:

Dichloro-5,12-dimethyl-1,5,8,12-tetraazabicyclo[6.6.2] hexadecane Manganese(II)
Dichloro-5,12-diethyl-1,5,8,12-tetraazabicyclo[6.6.2]hexadecane Manganese(II)
Diaquo-5,12-dimethyl-1,5,8,12-tetraazabicyclo[6.6.2]hexadecaneManganese(II) Hexafluorophosphate
Diaquo-5,12-diethyl-1,5,8,12-tetraazabicyclo[6.6.2]hexadecaneManganese(II) Hexafluorophosphate
Aquo-hydroxy-5,12-dimethyl-1,5,8,12-tetraazabicyclo [6.6.2]hexadecane Manganese(III) Hexafluorophosphate
Diaquo-5,12-dimethyl-1,5,8,12-tetraazabicyclo[6.6.2]hexadecaneManganese(II) Tetrafluoroborate
Dichloro-5,12-dimethyl-1,5,8,12 tetraazabicyclo[6.6.2] hexadecane Manganese(III) Hexafluorophosphate
Dichloro-5,12-diethyl-1,5,8,12-tetraazabicyclo[6.6.2]hexadecaneManganese(III) Hexafluorophosphate
Dichloro-5,12-di-n-butyl-1,5,8,12-tetraaza bicyclo[6.6.2] hexadecane Manganese(II)
Dichloro-5,12-dibenzyl-1,5,8,12-tetraazabicyclo[6.6.2] hexadecaneManganese(II)
Dichloro-5-n-butyl-12-methyl-1,5,8,12-tetraaza-bicyclo [6.6.2]hexadecane Manganese(II)
Dichloro-5-n-octyl-12-methyl-1,5,8,12-tetraaza-bicyclo [6.6.2]hexadecane Manganese(II)
Dichloro-5-n-butyl-12-methyl-1,5,8,12-tetraaza-bicyclo [6.6.2]hexadecane Manganese(II).

As a practical matter, and not by way of limitation, the compositions and methods herein can be adjusted to provide on the order of at least one part per hundred million of the active bleach catalyst species in the composition comprising a lipophilic fluid and a bleach system, and will preferably provide from about 0.01 ppm to about 25 ppm, more preferably from about 0.05 ppm to about 10 ppm, and most preferably from about 0.1 ppm to about 5 ppm, of the bleach catalyst species in the composition comprising a lipophilic fluid and a bleach system.

(d) Bleach Boosting Compounds

The compositions herein may comprise one or more bleach boosting compounds. Bleach boosting compounds provide increased bleaching effectiveness in lower temperature applications. The bleach boosters act in conjunction with conventional peroxygen bleaching sources to provide increased bleaching effectiveness. This is normally accomplished through in situ formation of an active oxygen transfer agent such as a dioxirane, an oxaziridine, or an oxaziridinium. Alternatively, preformed dioxiranes, oxaziridines and oxaziridiniums may be used.

Among suitable bleach boosting compounds for use in accordance with the present invention are cationic imines, zwitterionic imines, anionic imines and/or polyionic imines having a net charge of from about +3 to about −3, and mixtures thereof. These imine bleach boosting compounds of the present invention include those of the general structure:

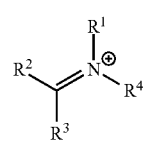

[I]

where $R^1$-$R^4$ may be a hydrogen or an unsubstituted or substituted radical selected from the group consisting of phenyl, aryl, heterocyclic ring, alkyl and cycloalkyl radicals.

Among preferred bleach boosting compounds are zwitterionic bleach boosters, which are described in U.S. Pat. Nos. 5,576,282 and 5,718,614. Other bleach boosting compounds include cationic bleach boosters described in U.S. Pat. Nos. 5,360,569; 5,442,066; 5,478,357; 5,370,826; 5,482,515; 5,550,256; and WO 95/13351, WO 95/13352, and WO 95/13353.

Peroxygen sources are well-known in the art and the peroxygen source employed in the present invention may comprise any of these well known sources, including peroxygen compounds as well as compounds, which under consumer use conditions, provide an effective amount of peroxygen in situ. The peroxygen source may include a hydrogen peroxide source, the in situ formation of a peracid anion through the reaction of a hydrogen peroxide source and a bleach activator, preformed peracid compounds or mixtures of suitable peroxygen sources. Of course, one of ordinary skill in the art will recognize that other sources of peroxygen may be employed without departing from the scope of the invention. The bleach boosting compounds, when present, are preferably employed in conjunction with a peroxygen source in the bleaching systems of the present invention.

(e) Preformed Peracids

Also suitable as bleaching agents are preformed peracids. The preformed peracid compound as used herein is any convenient compound which is stable and which under consumer use conditions provides an effective amount of peracid or peracid anion. The preformed peracid compound may be selected from the group consisting of percarboxylic acids and salts, percarbonic acids and salts, perimidic acids and salts, peroxymonosulfuric acids and salts, and mixtures thereof. Examples of these compounds are described in U.S. Pat. No. 5,576,282 to Miracle et al.

One class of suitable organic peroxycarboxylic acids have the general formula:

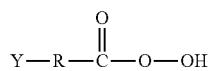

wherein R is an alkylene or substituted alkylene group containing from 1 to about 22 carbon atoms or a phenylene or substituted phenylene group, and Y is hydrogen, halogen, alkyl, aryl, —C(O)OH or —C(O)OOH.

Organic peroxyacids suitable for use in the present invention can contain either one or two peroxy groups and can be either aliphatic or aromatic. When the organic peroxycarboxylic acid is aliphatic, the unsubstituted peracid has the general formula:

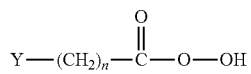

wherein Y can be, for example, H, $CH_3$, $CH_2Cl$, C(O)OH, or C(O)OOH; and n is an integer from 0 to 20. When the organic peroxycarboxylic acid is aromatic, the unsubstituted peracid has the general formula:

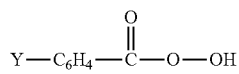

wherein Y can be, for example, hydrogen, alkyl, alkylhalogen, halogen, C(O)OH or C(O)OOH.

Typical monoperoxy acids useful herein include alkyl and aryl peroxyacids such as:
 (i) peroxybenzoic acid and ring-substituted peroxybenzoic acid, e.g. peroxy-a-naphthoic acid, monoperoxyphthalic acid (magnesium salt hexahydrate), and o-carboxybenzamidoperoxyhexanoic acid (sodium salt);
 (ii) aliphatic, substituted aliphatic and arylalkyl monoperoxy acids, e.g. peroxylauric acid, peroxystearic acid, N-nonanoylaminoperoxycaproic acid (NAPCA), N,N-(3-octylsuccinoyl)aminoperoxycaproic acid (SAPA) and N,N-phthaloylaminoperoxycaproic acid (PAP);
 (iii) amidoperoxyacids, e.g. mononoylamide of either peroxysuccinic acid (NAPSA) or of peroxyadipic acid (NAPAA).

Typical diperoxyacids useful herein include alkyl diperoxyacids and aryldiperoxyacids, such as:
 (i) 1,12-diperoxydodecanedioic acid;
 (ii) 1,9-diperoxyazelaic acid;
 (iii) diperoxybrassylic acid; diperoxysebacic acid and diperoxyisophthalic acid;
 (iv) 2-decyldiperoxybutane-1,4-dioic acid;
 (v) 4,4'-sulfonylbisperoxybenzoic acid.

Such bleaching agents are disclosed in U.S. Pat. Nos. 4,483,781 to Hartman and 4,634,551 to Burns et al.; European Patent Application 0,133,354 to Banks et al.; and U.S. Pat. No. 4,412,934 to Chung et al. Sources also include 6-nonylamino-6-oxoperoxycaproic acid as described in U.S. Pat. No. 4,634,551 to Burns et al. Persulfate compounds such as for example OXONE, manufactured commercially by E.I. DuPont de Nemours of Wilmington, Del. can also be employed as a suitable source of peroxymonosulfuric acid. PAP is disclosed in, for example, U.S. Pat. Nos. 5,487,818; 5,310,934; 5,246,620; 5,279,757 and 5,132,431.

(f) Photobleaches

Suitable photobleaches for use in the treating compositions of the present invention include, but are not limited to, the photobleaches described in U.S. Pat. Nos. 4,217,105 and 5,916,481.

(g) Enzyme Bleaching

Enzymatic systems may be used as bleaching agents. The hydrogen peroxide may also be present by adding an enzymatic system (i.e. an enzyme and a substrate therefore) which is capable of generating hydrogen peroxide at the beginning or during the washing and/or rinsing process. Such enzymatic systems are disclosed in EP Patent Application 91202655.6 filed Oct. 9, 1991.

The present invention compositions and methods may utilize alternative bleach systems such as ozone, chlorine dioxide and the like. Bleaching with ozone may be accomplished by introducing ozone-containing gas having ozone content from about 20 to about 300 g/m³ into the solution that is to contact the fabrics. The gas:liquid ratio in the solution should be maintained from about 1:2.5 to about 1:6. U.S. Pat. No. 5,346,588 describes a process for the utilization of ozone as an alternative to conventional bleach systems and is herein incorporated by reference.

The detergent compositions of the present invention may also include any number of additional optional ingredients. These include conventional laundry detergent composition components such as non-tinting dyes, detersive builders, enzymes, enzyme stabilizers (such as propylene glycol, boric acid and/or borax), suds suppressors, soil suspending agents, soil release agents, other fabric care benefit agents, pH adjusting agents, chelating agents, smectite clays, solvents, hydrotropes and phase stabilizers, structuring agents, dye transfer inhibiting agents, opacifying agents, optical brighteners, perfumes and coloring agents. The various optional detergent composition ingredients, if present in the compositions herein, should be utilized at concentrations conventionally employed to bring about their desired contribution to the composition or the laundering operation. Frequently, the total amount of such optional detergent composition ingredients can range from about 0.01% to about 50%, more preferably from about 0.1% to about 30%, by weight of the composition.

The liquid detergent compositions are in the form of an aqueous solution or uniform dispersion or suspension of surfactant, whitening agent, and certain optional other ingredients, some of which may normally be in solid form, that have been combined with the normally liquid components of the composition, such as the liquid alcohol ethoxylate nonionic, the aqueous liquid carrier, and any other normally liquid optional ingredients. Such a solution, dispersion or suspension will be acceptably phase stable and will typically have a viscosity which ranges from about 100 to 600 cps, more preferably from about 150 to 400 cps. For purposes of this invention, viscosity is measured with a Brookfield LVDV-II+ viscometer apparatus using a #21 spindle.

The liquid detergent compositions herein can be prepared by combining the components thereof in any convenient order and by mixing, e.g., agitating, the resulting component combination to form a phase stable liquid detergent composition. In a preferred process for preparing such compositions, a liquid matrix is formed containing at least a major proportion, and preferably substantially all, of the liquid components, e.g., nonionic surfactant, the non-surface active liquid carriers and other optional liquid components, with the liquid components being thoroughly admixed by imparting shear agitation to this liquid combination. For example, rapid stirring with a mechanical stirrer may usefully be employed. While shear agitation is maintained, substantially all of any anionic surfactants and the solid form ingredients can be added. Agitation of the mixture is continued, and if necessary, can be increased at this point to form a solution or a uniform dispersion of insoluble solid phase particulates within the liquid phase. After some or all of the solid-form materials have been added to this agitated mixture, particles of any enzyme material to be included, e.g., enzyme prills, are incorporated. As a variation of the composition preparation procedure hereinbefore described, one or more of the solid components may be added to the agitated mixture as a solution or slurry of particles premixed with a minor portion of one or more of the liquid components. After addition of all of the composition components, agitation of the mixture is continued for a period of time sufficient to form compositions having the requisite viscosity and phase stability characteristics. Frequently this will involve agitation for a period of from about 30 to 60 minutes.

In an alternate embodiment for forming the liquid detergent compositions, the whitening agent is first combined with one or more liquid components to form a whitening agent premix, and this whitening agent premix is added to a composition formulation containing a substantial portion, for example more than 50% by weight, more specifically, more than 70% by weight, and yet more specifically, more than 90% by weight, of the balance of components of the laundry detergent composition. For example, in the methodology described above, both the whitening agent premix and the enzyme component are added at a final stage of component additions. In a further embodiment, the whitening agent is encapsulated prior to addition to the detergent composition, the encapsulated whitening agent is suspended in a structured liquid, and the suspension is added to a composition formulation containing a substantial portion of the balance of components of the laundry detergent composition.

As noted previously, the detergent compositions may be in a solid form. Suitable solid forms include tablets and particulate forms, for example, granular particles or flakes. Various techniques for forming detergent compositions in such solid forms are well known in the art and may be used herein. In one embodiment, for example when the composition is in the form of a granular particle, the whitening agent is provided in particulate form, optionally including additional but not all components of the laundry detergent composition. The whitening agent particulate is combined with one or more additional particulates containing a balance of components of the laundry detergent composition. Further, the whitening agent, optionally including additional but not all components of the laundry detergent composition, may be provided in an encapsulated form, and the whitening agent encapsulate is combined with particulates containing a substantial balance of components of the laundry detergent composition.

The compositions of this invention, prepared as hereinbefore described, can be used to form aqueous washing solutions for use in the laundering of fabrics. Generally, an effective amount of such compositions is added to water, preferably in a conventional fabric laundering automatic washing machine, to form such aqueous laundering solutions. The aqueous washing solution so formed is then contacted, preferably under agitation, with the fabrics to be laundered therewith. An effective amount of the liquid detergent compositions herein added to water to form aqueous laundering solutions can comprise amounts sufficient to form from about 500 to 7,000 ppm of composition in aqueous washing solution. More preferably, from about 1,000 to 3,000 ppm of the detergent compositions herein will be provided in aqueous washing solution.

Fabric Care Compositions/Rinse Added Fabric Softening Compositions

In another specific embodiment, the whitening agents of the present invention may be included in a fabric care composition. The fabric care composition may be comprised of at least one whitening agent and a rinse added fabric softening composition ("RAFS;" also known as rinse added fabric conditioning compositions). Examples of typical rinse added softening compositions can be found in U.S. Provisional Patent Application Ser. No. 60/687,582 filed on Oct. 8, 2004. The rinse added fabric softening compositions of the present invention may comprise (a) fabric softening active and (b) a thiazolium dye. The rinse added fabric softening composition may comprise from about 1% to about 90% by weight of the FSA, more preferably from about 5% to about 50% by weight of the FSA. The whitening agent may be present in the rinse added fabric softening composition in an amount from about 0.5 ppb to about 50 ppm, more preferably from about 0.5 ppm to about 30 ppm.

In one embodiment of the invention, the fabric softening active (hereinafter "FSA") is a quaternary ammonium compound suitable for softening fabric in a rinse step. In one embodiment, the FSA is formed from a reaction product of a fatty acid and an aminoalcohol obtaining mixtures of mono-, di-, and, in one embodiment, triester compounds. In another embodiment, the FSA comprises one or more softener quaternary ammonium compounds such, but not limited to, as a monoalkyquaternary ammonium compound, a diamido quaternary compound and a diester quaternary ammonium compound, or a combination thereof.

In one aspect of the invention, the FSA comprises a diester quaternary ammonium (hereinafter "DQA") compound composition. In certain embodiments of the present invention, the DQA compounds compositions also encompasses a description of diamido FSAs and FSAs with mixed amido and ester linkages as well as the aforementioned diester linkages, all herein referred to as DQA.

A first type of DQA ("DQA (1)") suitable as a FSA in the present CFSC includes a compound comprising the formula:

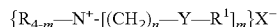

wherein each R substituent is either hydrogen, a short chain $C_1$-$C_6$, preferably $C_1$-$C_3$ alkyl or hydroxyalkyl group, e.g., methyl (most preferred), ethyl, propyl, hydroxyethyl, and the like, poly ($C_{2-3}$ alkoxy), preferably polyethoxy, group, benzyl, or mixtures thereof; each m is 2 or 3; each n is from 1 to about 4, preferably 2; each Y is —O—(O)C—, —C(O)—O—, —NR—C(O)—, or —C(O)—NR— and it is acceptable for each Y to be the same or different; the sum of carbons in each $R^1$, plus one when Y is —O—(O)C— or —NR—C(O)—, is $C_{12}$-$C_{22}$, preferably $C_{14}$-$C_{20}$, with each $R^1$ being a hydrocarbyl, or substituted hydrocarbyl group; it is acceptable for $R^1$ to be unsaturated or saturated and branched or linear and preferably it is linear; it is acceptable for each $R^1$ to be the same or different and preferably these are the same; and $X^-$ can be any softener-compatible anion, preferably, chloride, bromide, methylsulfate, ethylsulfate, sulfate, phosphate, and nitrate, more preferably chloride or methyl sulfate. Preferred DQA compounds are typically made by reacting alkanolamines such as MDEA (methyldiethanolamine) and TEA (triethanolamine) with fatty acids. Some materials that typically result from such reactions include N,N-di(acyl-oxyethyl)-N,N-dimethylammonium chloride or N,N-di(acyl-oxyethyl)-N,N-methylhydroxyethylammonium methylsulfate wherein the acyl group is derived from animal fats, unsaturated, and polyunsaturated, fatty acids, e.g., tallow, hardended tallow, oleic acid, and/or partially hydrogenated fatty acids, derived from vegetable oils and/or partially hydrogenated vegetable oils, such as, canola oil, safflower oil, peanut oil, sunflower oil, corn oil, soybean oil, tall oil, rice bran oil, palm oil, etc.

Non-limiting examples of suitable fatty acids are listed in U.S. Pat. No. 5,759,990 at column 4, lines 45-66. In one embodiment, the FSA comprises other actives in addition to DQA (1) or DQA. In yet another embodiment, the FSA comprises only DQA (1) or DQA and is free or essentially free of any other quaternary ammonium compounds or other actives. In yet another embodiment, the FSA comprises the precursor amine that is used to produce the DQA.

In another aspect of the invention, the FSA comprises a compound, identified as DTTMAC comprising the formula:

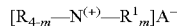

wherein each m is 2 or 3, each $R^1$ is a $C_6$-$C_{22}$, preferably $C_{14}$-$C_{20}$, but no more than one being less than about $C_{12}$ and then the other is at least about 16, hydrocarbyl, or substituted hydrocarbyl substituent, preferably $C_{10}$-$C_{20}$ alkyl or alkenyl (unsaturated alkyl, including polyunsaturated alkyl, also referred to sometimes as "alkylene"), most preferably $C_{12}$-$C_{18}$ alkyl or alkenyl, and branch or unbranched. In one embodiment, the Iodine Value (IV) of the FSA is from about 1 to 70; each R is H or a short chain $C_1$-$C_6$, preferably $C_1$-$C_3$ alkyl or hydroxyalkyl group, e.g., methyl (most preferred), ethyl, propyl, hydroxyethyl, and the like, benzyl, or $(R^2O)_{2-4}H$ where each $R^2$ is a $C_{1-6}$ alkylene group; and $A^-$ is a softener compatible anion, preferably, chloride, bromide, methylsulfate, ethylsulfate, sulfate, phosphate, or nitrate; more preferably chloride or methyl sulfate.

Examples of these FSAs include dialkydimethylammonium salts and dialkylenedimethylammonium salts such as ditallowedimethylammonium and ditallowedimethylammonium methylsulfate. Examples of commercially available dialkylenedimethylammonium salts usable in the present invention are di-hydrogenated tallow dimethyl ammonium chloride and ditallowedimethyl ammonium chloride available from Degussa under the trade names Adogen® 442 and Adogen® 470 respectively. In one embodiment, the FSA comprises other actives in addition to DTTMAC. In yet another embodiment, the FSA comprises only compounds of the DTTMAC and is free or essentially free of any other quaternary ammonium compounds or other actives.

In one embodiment, the FSA comprises an FSA described in U.S. Pat. Pub. No. 2004/0204337 A1, published Oct. 14, 2004 to Corona et al., from paragraphs 30-79. In another embodiment, the FSA is one described in U.S. Pat. Pub. No. 2004/0229769 A1, published Nov. 18, 2005, to Smith et al., on paragraphs 26-31; or U.S. Pat. No. 6,494,920, at column 1, line 51 et seq. detailing an "esterquat" or a quaternized fatty acid triethanolamine ester salt.

In one embodiment, the FSA is chosen from at least one of the following: ditallowoyloxyethyl dimethyl ammonium chloride, dihydrogenated-tallowoyloxyethyl dimethyl ammonium chloride, ditallow dimethyl ammonium chloride, ditallowoyloxyethyl dimethyl ammonium methyl sulfate, dihydrogenated-tallowoyloxyethyl dimethyl ammonium chloride, dihydrogenated-tallowoyloxyethyl dimethyl ammonium chloride, or combinations thereof.

In one embodiment, the FSA may also include amide containing compound compositions. Examples of diamide comprising compounds may include but not limited to methyl-bis (tallowamidoethyl)-2-hydroxyethylammonium methyl sulfate (available from Degussa under the trade names Varisoft 110 and Varisoft 222). An example of an amide-ester containing compound is N-[3-(stearoylamino)propyl]-N-[2-(stearoyloxy)ethoxy)ethyl)]-N-methylamine. Another specific embodiment of the invention provides for a rinse added fabric softening composition further comprising a cationic starch. Cationic starches are disclosed in US 2004/0204337 A1. In one embodiment, the rinse added fabric softening composition comprises from about 0.1% to about 7% of cationic starch by weight of the fabric softening composition. In one embodiment, the cationic starch is HCP401 from National Starch.

Suitable Laundry Care Ingredients

While not essential for the purposes of the present invention, the non-limiting list of laundry care ingredients illustrated hereinafter are suitable for use in the laundry care compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such ingredients are in addition to the components that were previously listed for any particular embodiment. The total amount of such adjuncts may range from about 0.1% to about 50%, or even from about 1% to about 30%, by weight of the laundry care composition.

The precise nature of these additional components, and levels of incorporation thereof, will depend on the physical form of the composition and the nature of the operation for which it is to be used. Suitable laundry care ingredients include, but are not limited to, polymers, for example cationic polymers, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the laundry care ingredients are not essential to Applicants' laundry care compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. However, when one or more adjuncts are present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Preferred transition-metals in the instant transition-metal bleach catalyst include manganese, iron and chromium. Preferred MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

EXAMPLES

The following examples are provided to further illustrate the novel whitening agents of the present invention; however, they are not to be construed as limiting the invention as defined in the claims appended hereto. In fact, it will be apparent to those skilled in the art that various modifications and variations can be made in this invention without departing from the scope or spirit of the invention. All parts and percents given in these examples are by weight unless otherwise indicated. All values of the Hansen Solubility Parameter reported herein are in units of $MPa^{0.5}$.

Sample Preparation and Test Methods

A. Sample Preparation

Each sample is prepared by adding 0.5 grams of whitening agent (0.1% based on weight of the cellulosic substrate) to a solution containing 3 grams of powdered laundry detergent (AATCC powder laundry detergent) and 500 mL of room temperature water. Each colorant loading is corrected for absorbance to assure equal amount of color units. The formulation is then combined with 50 grams of cellulose powder (available from Aldrich) and the mixture is agitated for 10 minutes. The mixture is then filtered to separate the cellulose particles from the liquid, and the cellulose particles are allowed to air dry. Both the cellulose particles and the liquid are measured for color using a Gretag Macbeth Color Eye 7000A spectrophotometer, as described previously.

The cellulose particles are then placed in a container containing 500 mL of tap water and agitated for 10 minutes. The mixture is filtered to separate the cellulose particles from the liquid, and the cellulose particles are again allowed to air dry. Both the cellulose particles and the liquid are again measured for color using the Gretag Macbeth Color Eye 7000A spectrophotometer. A Control Sample is also prepared that contained untreated cellulose particles (no whitening agent added).

The whitening agents shown in Tables 1A and 1B are prepared as described herein and tested for various parameters. All violet colorants are synthesized according to the procedure disclosed in U.S. Pat. No. 4,912,203 to Kluger et al. Note also that ethylene oxide, propylene oxide and butylenes oxide are shown below by their typical designation of "EO," "PO" and "BO," respectively. The average length and composition of the polymeric components of the whitening agents in Tables 1A and 1B is obtained from the formula: (Block 1+Block 2+Block 3)/(number of chains). For example, the average structure for Violet thiophene_5EO consists of a thiophene chromophore with 2 chains on the nitrogen, one equal to 3EO and one equal to 2EO. Chain caps are present on all polymeric components.

TABLE 1A

Identification of Inventive Whitening Agents

| Example No. | Sample Identification | Block 1 | Block 2 | Block 3 | # of Chains | Chain caps |
|---|---|---|---|---|---|---|
| Example 1 | Violet thiophene_3EO | 3 EO | — | — | 2 | OH |
| Example 2 | Violet thiophene_5EO | 5 EO | — | — | 2 | OH |
| Example 3 | Violet thiophene_10EO | 10 EO | — | — | 2 | OH |
| Example 4 | Violet thiophene_2EO_6PO | 2 EO | 6 PO | — | 2 | OH |
| Example 5 | Violet thiophene_5EO_5PO | 5 EO | 5 PO | — | 2 | OH |
| Example 6 | Violet thiophene_2EO_13PO | 2 EO | 13 PO | — | 2 | OH |
| Example 7 | Violet thiophene_2EO_14PO_8EO | 2 EO | 14 PO | 8 EO | 2 | OH |
| Example 8 | Violet thiophene_10EO_14PO | 10 EO | 14 PO | — | 2 | OH |
| Example 9 | Violet thiophene_10EO_8BO | 10 EO | 8 BO | — | 2 | OH |
| Example 10 | Violet thiophene_5EO_COCH$_2$CHRCOOH_RC$_8$H$_{17}$ | 5 EO | — | — | 2 | COCH$_2$CHRCOOHR=C$_8$H$_{17}$ |
| Example 11 | Violet thiophene_5EO_COCH$_3$ | 5EO | — | — | 2 | COCH$_3$ |
| Example 12 | Violet thiophene_glycidol | (CH$_2$CHOHCH$_2$OH)$_2$ | — | — | 2 | OH |
| Example 13 | Violet thiophene_glycidol_5EO$^{(a)}$ | (CH$_2$CHOHCH$_2$O—)$_2$ | 5 EO | — | 2 | OH |
| Example 14 | Violet thiophene_QUAT | [CH$_2$CHOHCH$_2$N$^+$(CH$_3$)$_3$]$_2$ | — | — | 2 | —N$^+$(CH$_3$)$_3$ |
| Example 15 | Triphenylmethane_10EO | (10 EO)$_2$ | — | — | 4 | OH |
| Example 16 | Triphenylmethane_30EO | (30 EO)$_2$ | — | — | 4 | OH |
| Example 17 | Triphenylmethane_2EO_2PO | (2EO)$_2$ | (2 PO)$_2$ | — | 4 | OH |

$^{(a)}$EO groups are added to the terminal OH group.

TABLE 1B

Identification of Inventive Whitening Agents

| Example No. | Sample Identification | Alky/aryl | Block 1 | Block 2 | Block 3 | # of Chains | Chain caps |
|---|---|---|---|---|---|---|---|
| Example 18 | Thiophene Violet N-Ethyl, N-glycidyl | CH$_2$CH$_3$ | (CH$_2$CHOHCH$_2$OH) | — | — | 2 | OH |

TABLE 1B-continued

Identification of Inventive Whitening Agents

| Example No. | Sample Identification | Alky/aryl | Block 1 | Block 2 | Block 3 | # of Chains | Chain caps |
|---|---|---|---|---|---|---|---|
| Example 19 | Thiophene Violet N-Ethyl, 5EO | $CH_2CH_3$ | 5EO | — | — | 1 | OH |
| Example 20 | Violet thiophene N,N-Bisglycidyl t-butyl ether 5 EO | — | $(CH_2CH(O-)CH_2OC(CH_3)_3)_2$ | 5EO | — | 2 | OH |
| Example 21 | Violet thiophene N,N-Bisglycidyl do/tetradecyl ether 5 ethoxylate | — | $(CH_2CH(O-)CH_2OC_{9,13}H_{18,26}CH_3)_2$ | 5EO | — | 2 | OH |
| Example 22 | Violet thiophene N,N-Bisglycidyl isopropyl ether 5 ethoxylate | — | $(CH_2CH(O-)CH_2OCH(C_2H_6))_2$ | — | — | 2 | OH |
| Example 23 | Violet thiophene N,N-Bisglycidyl n-butyl ether 5 ethoxylated | — | $(CH_2CH(O-)CH_2OCH_2CH_2CH_2CH_3)_2$ | — | — | 2 | OH |
| Example 24 | Violet thiophene N-Benzyl, 5-Ethoxylate | $CH_2C_6H_5$ | 5EO | — | — | 1 | OH |
| Example 25 | Violet thiophene N-Ethyl, N-t-butyl-glycidyl ether 5 ethoxylate | $CH_2CH_3$ | $CH_2CH(O-)CH_2OC(CH_3)_3$ | 5EO | — | 1 | OH |

(a) EO groups are added to the terminal OH group.

B. Calculation of Whiteness: CIELab b* and Ganz and CIE Whiteness Index

Whiteness Index ("WI") is a qualifying assessment of color that is calculated by a formula which includes three components of color measurement—hue, saturation, and lightness—which is then indexed to a standard white value. Several whiteness formulas can be used to measure whiteness on cellulose based substrates. Two common formulas are the Ganz Whiteness Index and CIE Whiteness. Ganz Whiteness Index is expressed by the formula: WI=(D*Y)+(P*x)+(Q*y)+C, where Y, x and y are colorimetric values and D, P, Q and C are formula parameters. CIE Whiteness is expressed by the formula: WI=Y−(800*x)−(1700*y)+813.7, where Y, x and y are colorimetric values. Further information is available in the publication of Rolf Griesser, Ciba-Geigy Ltd, "Whiteness and Tint", June 1993.

The surface color of an article may be quantified using a series of measurements—L*, a*, and b*—generated by measuring the samples using a spectrophotometer. The equipment used for this test is a Gretag Macbeth Color Eye 7000A spectrophotometer. The software program used is "Color imatch." "L" is a measure of the amount of white or black in a sample; higher "L" values indicate a lighter colored sample. A measure of the amount of red or green in a sample is determined by "a*" values. A measure of the amount of blue or yellow in a sample is determined by "b*" values; lower (more negative) b* values indicate more blue on a sample.

Yet another measurement of the relative color of a substrate is DE CMC. DE CMC is a measure of the overall color difference for all uniform color spaces, where DE CMC represents the magnitude of difference between a color and a reference (in this case, a pure white standard). The higher the DE CMC value, the more pronounced the difference in color. In other words, smaller DE CMC values represent colors that are closer to white. The Gretag Macbeth Color Eye 7000A Spectrophotometer calculates DE CMC values based on wavelength and reflectance data for each sample.

C. Calculation of Molecular Properties

The average structure of each inventive whitening agent is drawn with Material Studio molecular modeling software (available from Accelrys, Inc.). Each structure's geometry is optimized by minimizing its energy with the Forcite module using the semi-empirical Universal forcefield and the Qeq charge assignment system. The N=N bond of the diazo colorants are calculated at ~1.270-1.275 Angstroms compared to the average N=N bond distance of 1.25 Angstroms. These values are slightly shorter that those reported by Liu Jun-na et al., i.e., ~1.3 angstroms, which are calculated for diphenyl diazo dyes with Gaussian 98 software package and the B3LYP/6-311G method (Liu Jun-na, Chen Zhi-rong, and Yuan Shen-feng, Journal of Zhejiang University Science, 6B(6), 2005, pp. 584-589).

After the geometry optimization of all structures, a variety of descriptors are calculated. Descriptors can be categorized in the following categories: 1. Structural, 2. Functional, 3. Energetic, 4. Topological, 5. Spatial, and 6. Thermodynamic.

All descriptors are calculated with the QSAR module of Material Studio software, except for the total number of EO groups and PO groups on the chromophore, the Hansen solubility parameter (Solubility_parameter), and the Hydrophile-Lipophile Balance number (MW_HLB). The latter two parameters are calculated with ChemSW's Molecular Modeling Pro software. Descriptors are screened as potential predictors of affinity of the whitening agent to the cellulosic substrate. Table 2 summarizes some of the test parameters that are used to characterize the whitening agents of the present invention.

TABLE 2

Summary of Test Parameters

| Descriptor Symbol | Test Name | Definition |
|---|---|---|
| Hansen Solubility parameter, $\delta$ | Hansen total (Hildebrand) solubility | $\delta^2 = \delta^2_{dispersion} + \delta^2_{polar} + \delta^2_{H\text{-}bonding}$ sum of solubility components for dispersion, polarity, and hydrogen bonding forces, respectively |
| FPSA1 (Jurs descriptor) | Fractional Positive Surface Area | Sum of the solvent-accessible surface area of all positively-charged atoms divided by total molecular solvent-accessible surface area |
| RPSA (Jurs descriptor) | Relative Polar Surface Area | Total polar surface area divided by total molecular solvent-accessible surface area |
| Radius of Gyration | Parameter characterizing the size of any shape | $(\Sigma m_i r_i^2 / \Sigma m_i)^{0.5}$, where $m_i$ = mass of element i, $r_i$ = distance of element from center of mass |
| Dipole Moment Magnitude | Magnitude of dipole moment from spatial descriptor set | $\Sigma q_i r_i$, where $q_i$ = partial atomic charge, $r_i$ = distance |
| Polarizability | Sum of atomic polarizabilities | relative tendency of the electron cloud of a molecule to be distorted from its normal shape by the presence of a nearby ion or dipole |

Test Results

Test 1: Whiteness Test As Determined by CIELab b* Values and the Ganz Whiteness Index Examples 1 through 17 are tested for whiteness to determine CIELab b* values and Ganz Whiteness Index ("Ganz WI") values. Test results are provided in Table 3. Lower (more negative) CIELab b* values and higher positive Ganz WI values indicate that more blueing, or whitening effect, is exhibited by the treated cellulose particles.

TABLE 3

Test Results For Whiteness as Determined by CIELab b* Values and the Ganz Whiteness Index

| Sample | CIELab b* Color Value Post Rinse 1 | Ganz Whiteness Index Value Post Rinse 1 |
|---|---|---|
| Control | 2.66 | 54.34 |
| Example 1 | −7.57 | 144.11 |
| Example 2 | −9.28 | 162.21 |
| Example 3 | −5.34 | 118.09 |
| Example 4 | −6.58 | 135.30 |
| Example 5 | −4.12 | 107.80 |
| Example 6 | −3.49 | 102.93 |
| Example 7 | −4.57 | 113.82 |
| Example 8 | −3.19 | 101.29 |
| Example 9 | −3.58 | 102.75 |
| Example 10 | −5.76 | 127.03 |
| Example 11 | −4.48 | 112.85 |
| Example 12 | −9.37 | 162.00 |
| Example 13 | −5.94 | 126.34 |
| Example 14 | −5.36 | 119.92 |
| Example 15 | −5.46 | 125.44 |
| Example 16 | −3.69 | 107.50 |
| Example 17 | −6.51 | 135.99 |

The test results indicate that Example 2, which contained 5 ethylene oxide repeating units, and Example 12, which contained a glycidol unit, performed the best under these test conditions. The data reveals a relatively linear correlation between CIELab b* color values and the Ganz WI values. A linear regression fit for all of the data points has a regression value of $R^2=0.988$.

Test 2: Measurement of CIELab b* Values and the Dispersion Component Values of Hansen Solubility Parameter Examples 1 through 17 are tested to determine CIELab b* values and the dispersion component values of the Hansen Solubility Parameter. Note that Examples 1 through 14 contain a violet thiophene chromophore, while Examples 15 through 17 contain triphenylmethane colorants. Examples 18 through 25 are tested to determine the dispersion component value of the Hansen Solubility Parameter only.

Test results are provided in Table 4. Larger negative CIELab b* values indicate that more blueing, or whitening effect, is exhibited by the treated cellulose particles. "N/A" indicates that data are not available.

TABLE 4

Measured CIELab b* Values and Dispersion Component Values of Hansen Solubility Parameter

| Sample | CIELab b* Color Value Post Rinse 1 | Dispersion Component Value of Hansen Solubility Parameter ($MPa^{0.5}$) Post Rinse 1 |
|---|---|---|
| Control | 2.66 | 25.4 |
| Example 1 | −7.57 | 14.9 |
| Example 2 | −9.28 | 14.8 |
| Example 3 | −5.34 | 16.6 |
| Example 4 | −6.58 | 17.9 |
| Example 5 | −4.12 | 18.4 |
| Example 6 | −3.49 | 18.5 |
| Example 7 | −4.57 | 18.2 |
| Example 8 | −3.19 | 19.1 |
| Example 9 | −3.58 | 18.6 |
| Example 10 | −5.76 | 18.5 |
| Example 11 | −4.48 | 19.6 |
| Example 12 | −9.37 | 14.1 |
| Example 13 | −5.94 | 12.7 |
| Example 14 | −5.36 | 16.8 |
| Example 15 | −5.46 | 16.8 |
| Example 16 | −3.69 | 19.5 |
| Example 17 | −6.51 | 18.5 |
| Example 18 | N/A | 16.3 |
| Example 19 | N/A | 16.7 |
| Example 20 | N/A | 15.8 |

TABLE 4-continued

Measured CIELab b* Values and Dispersion Component Values of Hansen Solubility Parameter

| Sample | CIELab b* Color Value Post Rinse 1 | Dispersion Component Value of Hansen Solubility Parameter (MPa$^{0.5}$) Post Rinse 1 |
|---|---|---|
| Example 21 | N/A | 16.6 |
| Example 22 | N/A | 16.0 |
| Example 23 | N/A | 16.2 |
| Example 24 | N/A | 17.0 |
| Example 25 | N/A | 16.4 |

The test results reveal a relatively linear correlation between the blueing parameter, CIELab b*, and the dispersion component value of the Hansen Solubility Parameter. The color value b* decreases (i.e. blueing performance increases) linearly as $\delta_d$ decreases.

A linear regression fit for all of the data points and has a regression value of $R^2$=0.763. The regression line has the following equation:

$$b\_blueing = 0.9704 * \delta_d - 22.468 \quad (2)$$

Test 3: Prediction of CIELab b* Values Based on the Dispersion Component Values of Hansen Solubility Parameter Examples 1-10 and 15-17 are first used to train a model based on the dispersion component value of the Hansen Solubility Parameter. The CIELab b* value is calculated for these Examples using Equation 3, as shown below, which utilizes the dispersion component value obtained after 1 rinse cycle:

$$b\_blueing = 1.0014 * \delta_d - 23.02 \quad (3)$$

This equation is very similar to Equation 2, which is derived using all of the Examples. The model represented by Equation 3 is validated with test compounds in Examples 11-14. Equation 3 is used to generate predictions for the CIELab b* value of molecules in Examples 11-14 (test molecules) before these molecules are synthesized and tested for whitening efficiency. The predicted CIELab b* values obtained from Equation 3 are compared to the measured values previously obtained from the Gretag Macbeth Color Eye 7000A spectrophotometer. The percent difference between measured b* color values and predicted b* color values is also determined.

Dispersion component values and predicted CIELab b* values are also determined for Comparative Examples 1 and 2. Comparative Example 1 is a blue polymeric anthraquinone dye disclosed in Example III of U.S. Pat. No. 4,127,243 to Farmer. Comparative Example 2 is Basic Violet 3, as disclosed in Table 2 of US Patent Application Publication No. 2005/0288206 to Sadlowski et al.

Test results are provided in Table 5 and FIG. 1. "N/A" indicates that data are not available.

TABLE 5

Predicted CIELab b* Values Based on Dispersion Component Values of Hansen Solubility Parameter After Post Rinse 1

| Example No. | Dispersion Component Value of Hansen Solubility Parameter (MPa$^{0.5}$) | Predicted CIELab b* Value | Measured CIELab b* Value | Difference Between Predicted and Measured CIELab b* Values (%) |
|---|---|---|---|---|
| Control | 25.4 | N/A | 2.66 | N/A |
| Example 1 | 14.9 | −8.1 | −7.57 | 6.6 |
| Example 2 | 14.8 | −8.2 | −9.28 | −13.2 |
| Example 3 | 16.6 | −6.4 | −5.34 | 17.0 |
| Example 4 | 17.9 | −5.1 | −6.58 | −29.9 |
| Example 5 | 18.4 | −4.6 | −4.12 | 10.6 |
| Example 6 | 18.5 | −4.5 | −3.49 | 22.2 |
| Example 7 | 18.2 | −4.8 | −4.57 | 5.0 |
| Example 8 | 19.1 | −3.8 | −3.19 | 16.4 |
| Example 9 | 18.6 | −4.4 | −3.58 | 19.3 |
| Example 10 | 18.5 | −4.5 | −5.76 | −27.6 |
| Example 11 | 19.6 | −4.3 | −4.48 | −3.8 |
| Example 12 | 14.1 | −8.9 | −9.37 | −4.9 |
| Example 13 | 12.7 | −8.7 | −8.25 | 5.2 |
| Example 14 | 16.8 | −6.2 | −5.32 | 14.4 |
| Example 15 | 16.8 | −6.2 | −5.46 | 12.3 |
| Example 16 | 19.5 | −3.5 | −3.69 | −4.7 |
| Example 17 | 18.5 | −4.4 | −6.51 | −46.4 |
| Comparative Example 1 | 21.3 | −1.7 | N/A | N/A |
| Comparative Example 2 | 19.5 | −3.5 | N/A | N/A |

Example 11 (Violet thiophene_5EO_COCH3) and Example 12 (Violet thiophene_glycidol) are synthesized and tested to verify that the model can explain the effects of the functionality of the polymeric chain end caps. Example 12 has four hydroxyl groups, while whitening agents with EO or PO end groups have only 2 hydroxyl groups. Example 11 has roughly the same size as Example 12, but the acetate caps are less polar than the OH groups.

FIG. 1 provides a graphical representation of the data. The phrase "violet thiophene" is shown as "violet" and "triphenylmethane" is shown as "TPM" on FIG. 1. The data points represent the measured CIELab b* color values. The solid line represents Equation 3, which is the predicted data. The linear correlation between color value b* and $\delta_d$ suggests that the smaller the molecule the stronger the deposition on the cellulose powder. The size of the whitening agent compound may influence its ability to access and diffuse into the pores of the cellulose powder. In addition, whitening agents having a more polar cap on the chains of the molecule, or those whitening agents having a greater number of polar end groups, exhibited greater blueing efficacy. The calculations also show that triphenylmethane-containing whitening agents are preferred whitening agents.

Exemplary Detergent Formulations

Formulations 1a-1l: Liquid Detergent Formulations

Tables 6A and 6B provide examples of liquid detergent formulations which include at least one whitening agent of the present invention. The formulations are shown in Table 6A as Formulations 1a through 1f and in Table 6B as Formulations 1 g through 1l.

TABLE 6A

Liquid Detergent Formulations Comprising the Inventive Whitening Agent

| Ingredient | 1a wt % | 1b wt % | 1c wt % | 1d wt % | 1e wt % | 1f[5] wt % |
|---|---|---|---|---|---|---|
| sodium alkyl ether sulfate | 14.4% | 14.4% | | 9.2% | 5.4% | |
| linear alkylbenzene sulfonic acid | 4.4% | 4.4% | 12.2% | 5.7% | 1.3% | 22.0% |
| alkyl ethoxylate | 2.2% | 2.2% | 8.8% | 8.1% | 3.4% | 18.0% |
| amine oxide | 0.7% | 0.7% | 1.5% | | | |
| citric acid | 2.0% | 2.0% | 3.4% | 1.9% | 1.0% | 1.6% |
| fatty acid | 3.0% | 3.0% | 8.3% | | | 16.0% |
| protease | 1.0% | 1.0% | 0.7% | 1.0% | | 2.5% |
| amylase | 0.2% | 0.2% | 0.2% | | | 0.3% |
| lipase | | | | 0.2% | | |
| borax | 1.5% | 1.5% | 2.4% | 2.9% | | |
| calcium and sodium formate | 0.2% | 0.2% | | | | |
| formic acid | | | | | | 1.1% |
| amine ethoxylate polymers | 1.8% | 1.8% | 2.1% | | | 3.2% |
| sodium polyacrylate | | | | | 0.2% | |
| sodium polyacrylate copolymer | | | | 0.6% | | |
| DTPA[1] | 0.1% | 0.1% | | | | 0.9% |
| DTPMP[2] | | | 0.3% | | | |
| EDTA[3] | | | | | 0.1% | |
| fluorescent whitening agent | 0.15% | 0.15% | 0.2% | 0.12% | 0.12% | 0.2% |
| ethanol | 2.5% | 2.5% | 1.4% | 1.5% | | |
| propanediol | 6.6% | 6.6% | 4.9% | 4.0% | | 15.7% |
| sorbitol | | | | 4.0% | | |
| ethanolamine | 1.5% | 1.5% | 0.8% | 0.1% | | 11.0% |
| sodium hydroxide | 3.0% | 3.0% | 4.9% | 1.9% | 1.0% | |
| sodium cumene sulfonate | | | 2.0% | | | |
| silicone suds suppressor | | | 0.01% | | | |
| perfume | 0.3% | 0.3% | 0.7% | 0.3% | 0.4% | 0.6% |
| Example 15 table 1 | | 0.001% | | | 0.0005% | |
| Example 2 table 1 | 0.013% | | 0.005% | 0.003% | | 0.001% |
| water | balance | balance | balance | balance | balance | balance |
| | 100.0% | 100.0% | 100.0% | 100.0% | 100.0% | 100.0% |

TABLE 6B

Liquid Detergent Formulations Comprising the Inventive Whitening Agent

| Ingredient | 1g wt % | 1h wt % | 1i wt % | 1j wt % | 1k wt % | 1l[6] wt % |
|---|---|---|---|---|---|---|
| sodium alkyl ether sulfate | 14.4% | 14.4% | | 9.2% | 5.4% | |
| linear alkylbenzene sulfonic acid | 4.4% | 4.4% | 12.2% | 5.7% | 1.3% | 22.0% |
| alkyl ethoxylate | 2.2% | 2.2% | 8.8% | 8.1% | 3.4% | 18.0% |
| amine oxide | 0.7% | 0.7% | 1.5% | | | |
| citric acid | 2.0% | 2.0% | 3.4% | 1.9% | 1.0% | 1.6% |
| fatty acid | 3.0% | 3.0% | 8.3% | | | 16.0% |
| protease | 1.0% | 1.0% | 0.7% | 1.0% | | 1.7% |
| amylase | 0.2% | 0.2% | 0.2% | | | 0.6% |
| lipase | | | | 0.2% | | 0.2% |
| borax | 1.5% | 1.5% | 2.4% | 2.9% | | |
| calcium and sodium formate | 0.2% | 0.2% | | | | |
| formic acid | | | | | | 1.1% |
| amine ethoxylate polymers | 1.8% | 1.8% | 2.1% | | | 3.2% |
| sodium polyacrylate | | | | | 0.2% | |
| sodium polyacrylate copolymer | | | | 0.6% | | |
| DTPA[1] | 0.1% | 0.1% | | | | 0.9% |
| DTPMP[2] | | | 0.3% | | | |
| EDTA[3] | | | | | 0.1% | |
| fluorescent whitening agent | 0.15% | 0.15% | 0.2% | 0.12% | 0.12% | 0.2% |
| ethanol | 2.5% | 2.5% | 1.4% | 1.5% | | |
| propanediol | 6.6% | 6.6% | 4.9% | 4.0% | | 15.7% |
| sorbitol | | | | 4.0% | | |
| ethanolamine | 1.5% | 1.5% | 0.8% | 0.1% | | 11.0% |
| sodium hydroxide | 3.0% | 3.0% | 4.9% | 1.9% | 1.0% | |
| sodium cumene sulfonate | | | 2.0% | | | |

TABLE 6B-continued

Liquid Detergent Formulations Comprising the Inventive Whitening Agent

| Ingredient | 1g wt % | 1h wt % | 1i wt % | 1j wt % | 1k wt % | 1l[6] wt % |
|---|---|---|---|---|---|---|
| silicone suds suppressor | | | 0.01% | | | |
| perfume | 0.3% | 0.3% | 0.7% | 0.3% | 0.4% | 0.6% |
| Example 15 table 1 | 0.01% | | | | 0.005% | |
| Example 2 table 1 | | 0.01% | 0.02% | 0.003% | | 0.012% |
| opacifier[9] | | 0.5% | | | | |
| water | balance | balance | balance | balance | balance | balance |
| | 100.0% | 100.0% | 100.0% | 100.0% | 100.0% | 100.0% |

Footnotes for Formulations 1a-1:
[1] diethylenetriaminepentaacetic acid, sodium salt
[2] diethylenetriaminepentakismethylenephosphonic acid, sodium salt
[3] ethylenediaminetetraacetic acid, sodium salt
[4] a non-tinting dyes used to adjust formula color
[5] compact formula, packaged as a unitized dose in polyvinyl alcohol film
[6] alkoxylated anthraquinone colorant with hueing efficiency >10 and wash removability 30-85%
[7] alkoxylated thiophene colorant with hueing efficiency >10 and wash removability 30-85%
[8] alkoxylated triphenylmethane colorant with hueing efficiency >10 and wash removability 30-85%
[9] Acusol OP301

Formulations 2a-2e: Granular Detergent Formulations

Table 7 provides examples of granular detergent formulations which include at least one whitening agent of the present invention. The formulations are shown in Table 7 as Formulations 2a through 2e.

TABLE 7

Granular Detergent Formulations Comprising the Inventive Whitening Agent

| Ingredient | 2a wt % | 2b wt % | 2c wt % | 2d wt % | 2e wt % |
|---|---|---|---|---|---|
| Na linear alkylbenzene sulfonate | 3.4% | 3.3% | 11.0% | 3.4% | 3.3% |
| Na alkylsulfate | 4.0% | 4.1% | | 4.0% | 4.1% |
| Na alkyl sulfate (branched) | 9.4% | 9.6% | | 9.4% | 9.6% |
| alkyl ethoxylate | | | 3.5% | | |
| type A zeolite | 37.4% | 35.4% | 26.8% | 37.4% | 35.4% |
| sodium carbonate | 22.3% | 22.5% | 35.9% | 22.3% | 22.5% |
| sodium sulfate | 1.0% | | 18.8% | 1.0% | |
| sodium silicate | | | 2.2% | | |
| protease | 0.1% | 0.2% | | 0.1% | 0.2% |
| sodium polyacrylate | 1.0% | 1.2% | 0.7% | 1.0% | 1.2% |
| carboxymethylcellulose | | | 0.1% | | |
| PEG 600 | | 0.5% | | | 0.5% |
| PEG 4000 | | 2.2% | | | 2.2% |
| DTPA | 0.7% | 0.6% | | 0.7% | 0.6% |
| fluorescent whitening agent | 0.1% | 0.1% | 0.1% | 0.1% | 0.1% |
| sodium percarbonate | | 5.0% | | | 5.0% |
| sodium nonanoyloxybenzenesulfonate | | 5.3% | | | 5.3% |
| silicone suds suppressor | 0.02% | 0.02% | | 0.02% | 0.02% |
| perfume | 0.3% | 0.3% | 0.2% | 0.3% | 0.3% |
| Example 15 table 1 | 0.004% | | | | 0.02% |
| Example 2 table 1 | | 0.006% | 0.002% | 0.004% | |
| water and miscellaneous | balance | balance | balance | balance | balance |
| | 100.0% | 100.0% | 100.0% | 100.0% | 100.0% |

Exemplary Fabric Care Compositions

Formulations 3a-3d: Liquid Fabric Care Compositions

Table 8 provides examples of liquid fabric care compositions which include at least one whitening agent of the present invention. The compositions are shown in Table 8 as Formulations 3a through 3d.

TABLE 8

Liquid Fabric Care Compositions Comprising the Inventive Whitening Agent

| Ingredients | 3a | 3b | 3c | 3d |
|---|---|---|---|---|
| Fabric Softening Active[a] | 13.70% | 13.70% | 13.70% | 13.70% |
| Ethanol | 2.14% | 2.14% | 2.14% | 2.14% |
| Cationic Starch[b] | 2.17% | 2.17% | 2.17% | 2.17% |

TABLE 8-continued

Liquid Fabric Care Compositions Comprising the Inventive Whitening Agent

| Ingredients | 3a | 3b | 3c | 3d |
|---|---|---|---|---|
| Perfume | 1.45% | 1.45% | 1.45% | 1.45% |
| Phase Stabilizing Polymer[c] | 0.21% | 0.21% | 0.21% | 0.21% |
| Calcium Chloride | 0.147% | 0.147% | 0.147% | 0.147% |
| DTPA[d] | 0.007% | 0.007% | 0.007% | 0.007% |
| Preservative[e] | 5 ppm | 5 ppm | 5 ppm | 5 ppm |
| Antifoam[f] | 0.015% | 0.015% | 0.015% | 0.015% |
| Example 1 of Table 1 | 30 ppm | | | 15 ppm |
| Example 2 of Table 1 | | 30 ppm | | |
| Example 3 of Table 1 | | | 30 ppm | 15 ppm |
| Tinopal CBS-X[g] | 0.2 | 0.2 | 0.2 | 0.2 |
| Ethoquad C/25[h] | 0.26 | 0.26 | 0.26 | 0.26 |
| Ammonium Chloride | 0.1% | 0.1% | 0.1% | 0.1% |
| Hydrochloric Acid | 0.012% | 0.012% | 0.012% | 0.012% |
| Deionized Water | Balance | Balance | Balance | Balance |

[a]N,N-di(tallowoyloxyethyl)-N,N-dimethylammonium chloride.
[b]Cationic starch based on common maize starch or potato starch, containing 25% to 95% amylose and a degree of substitution of from 0.02 to 0.09, and having a viscosity measured as Water Fluidity having a value from 50 to 84.
[c]Copolymer of ethylene oxide and terephthalate having the formula described in U.S. Pat. No. 5,574,179 at col.15, lines 1-5, wherein each X is methyl, each n is 40, u is 4, each $R^1$ is essentially 1,4-phenylene moieties, each $R^2$ is essentially ethylene, 1,2-propylene moieties, or mixtures thereof.
[d]Diethylenetriaminepentaacetic acid.
[e]KATHON ® CG available from Rohm and Haas Co.
[f]Silicone antifoam agent available from Dow Corning Corp. under the trade name DC2310.
[g]Disodium 4,4'-bis-(2-sulfostyryl) biphenyl, available from Ciba Specialty Chemicals.
[h]Cocomethyl ethoxylated [15] ammonium chloride, available from Akzo Nobel.

Accordingly, the present invention provides a whitening agent for cellulosic substrates comprising at least one chromophore component that comprises a thiophene or triphenylmethane colorant and at least one polymeric component; wherein the whitening agent possesses a dispersion component value of the Hansen Solubility Parameter of less than or equal to about 17 MPa$^{0.5}$. A laundry detergent containing such a whitening agent is also contemplated herein.

The whitening agent of the present invention includes a whitening agent for cellulosic substrates comprising at least one chromophore component that comprises a thiophene colorant and at least one polymeric component wherein the whitening agent is characterized by the following structure:

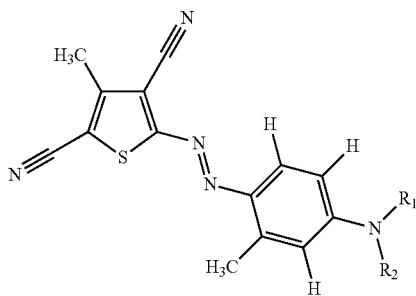

Wherein $R_1$ and $R_2$ can independently be selected from:
a) $[(CH_2CR'HO)_x(CH_2CR''HO)_yH]$
   wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein $x+y \leq 5$; wherein $y \geq 1$; and wherein z=0 to 5;
b) $R_1$=alkyl, aryl or aryl alkyl and $R_2=[(CH_2CR'HO)_x(CH_2CR''HO)_yH]$
   wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein $x+y \leq 10$; wherein $y \geq 1$; and wherein z=0 to 5;
c) $R_1=[CH_2CH_2(OR_3)CH_2OR_4]$ and $R_2=[CH_2CH_2(OR_3)CH_2OR_4]$
   wherein $R_3$ is selected from the group consisting of H, $(CH_2CH_2O)_zH$, and mixtures thereof; and wherein z=0 to 10;
   wherein $R_4$ is selected from the group consisting of ($C_1$-$C_{16}$)alkyl, aryl groups, and mixtures thereof; and
d) wherein R1 and R2 can independently be selected from the amino addition product of styrene oxide, glycidyl methyl ether, isobutyl glycidyl ether, isopropylglycidyl ether, t-butyl glycidyl ether, 2-ethylhexylgycidyl ether, and glycidylhexadecyl ether, followed by the addition of from 1 to 10 alkylene oxide units.

A potentially preferred whitening agent of the present invention includes a whitening agent for cellulosic substrates comprising at least one chromophore component that comprises a thiophene colorant and at least one polymeric component wherein the whitening agent is characterized by the following structure:

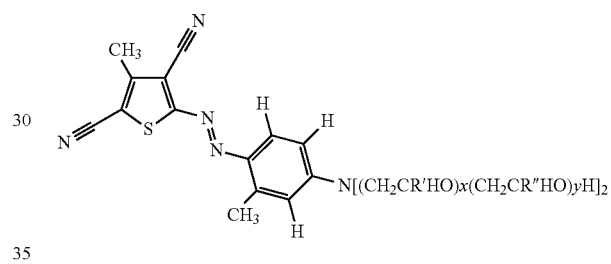

wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein $x+y \leq 5$; wherein $y \geq 1$; and wherein z=0 to 5.

Additionally, the present invention provides a whitening agent characterized by a CIELab b* color value ("b") and a dispersion component value of the Hansen Solubility Parameter ("$\delta_d$"), wherein "b" and "$\delta_d$" exhibit an approximately linear correlation with each other according to the following equation: $b=1.00(\delta_d)-23$. A laundry detergent containing such a whitening agent is also contemplated herein.

Thus, it is believed to be an advantage of the present invention to employ the predictive model to aid in the selection of chromophore-containing compounds ideally suited as whitening agents. Test results provided herein tend to indicate that deposition of the whitening agent on the cellulose powder may be controlled, at least in part, by the size of the whitening agent compound and by its chain cap functionality. Test results also suggest that larger molecules may be too bulky to diffuse into the pores of the cellulose powder which may decrease the whitening effect after multiple washing and/or rinsing cycles.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A laundry care composition comprising a laundry care ingredient and a whitening agent for cellulosic substrates, said whitening agent comprising:
    (a) at least one chromophore component that comprises a thiophene colorant, and
    (b) at least one polymeric component;
    wherein the whitening agent is characterized by the following structure:

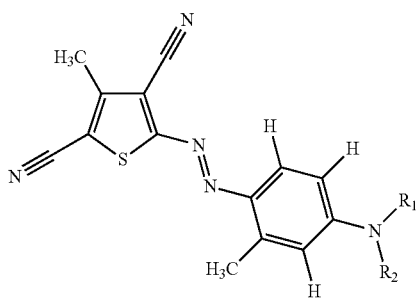

Wherein $R_1$ and $R_2$ can independently be selected from:
   a) $[(CH_2CR'HO)_x(CH_2CR''HO)_yH]$
        wherein R' is selected from the group consisting of H, $CH_3$, $CH_2O(CH_2CH_2O)_zH$; wherein R'' is selected from the group consisting of H, $CH_2O(CH_2CH_2O)_zH$, and mixtures thereof; wherein x=0; wherein x+y≦5; wherein y≧1; and wherein z=0 to 5;
   b) $R_1$=alkyl, aryl or aryl alkyl and $R_2$=$[(CH_2CR'HO)_x(CH_2CR''HO)_yH]$
        wherein R' is selected from the group consisting of H, $CH_3$, $CH_2O(CH_2CH_2O)_zH$, and mixtures thereof; wherein R'' is selected from the group consisting of H, $CH_2O(CH_2CH_2O)_zH$, and mixtures thereof; wherein x+y≦10; wherein y≧1; and wherein z=0 to 5;
   c) $R_1$=$[CH_2CH(OR_3)CH_2OR_4]$ and $R_2$=$[CH_2CH(OR_3)CH_2OR_4]$
        wherein $R_3$ is selected from the group consisting of H, $(CH_2CH_2O)_zH$; and
        wherein z=0 to 10;
        wherein $R_4$ is selected from the group consisting of $(C_1-C_{16})$alkyl, aryl groups.

2. The laundry care composition of claim 1 wherein $R_1$ and $R_2$ can independently be selected from the amino addition product of styrene oxide, glycidyl methyl ether, isobutyl glycidyl ether, isopropylglycidyl ether, t-butyl glycidyl ether, 2-ethylhexylgycidyl ether, and glycidylhexadecyl ether, followed by the addition of from 1 to 10 alkylene oxide units.

3. The laundry care composition of claim 1, wherein the whitening agent comprises a polyoxyalkylene chain having from 2 to about 20 repeating units.

4. The laundry care composition of claim 1, wherein the whitening agent comprises at least two hydroxyl groups.

5. The laundry care composition of claim 4, wherein the hydroxyl groups are primary hydroxyl moieties.

6. The laundry care composition of claim 1, wherein the whitening agent possesses a dispersion component value of the Hansen Solubility Parameter of less than or equal to about 17 $MPa^{0.5}$.

7. The laundry care composition of claim 6, wherein the whitening agent possesses a dispersion component value of the Hansen Solubility Parameter from about 12 to about 17 $MPa^{0.5}$.

8. The laundry care composition of claim 1, wherein the whitening agent's chromophore exhibits an absorbance spectrum in water of from about 520 nanometers to about 640 nanometers.

9. The laundry care composition of claim 1, wherein the whitening agent's chromophore exhibits an emission spectrum in water of from about 400 nanometers to about 480 nanometers.

* * * * *